United States Patent
Quinn et al.

(10) Patent No.: US 7,105,170 B2
(45) Date of Patent: Sep. 12, 2006

(54) LATENT HUMAN TUBERCULOSIS MODEL, DIAGNOSTIC ANTIGENS, AND METHODS OF USE

(75) Inventors: Frederick D. Quinn, Avondale Estates, GA (US); Kristin A. Birkness, Atlanta, GA (US); Manon Deslauriers, Quebec City (CA); Peter King, Nacogdoches, TX (US); David S. Beall, Atlantic Beach, FL (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/250,930

(22) PCT Filed: Jan. 7, 2002

(86) PCT No.: PCT/US02/00309

§ 371 (c)(1),
(2), (4) Date: Feb. 17, 2004

(87) PCT Pub. No.: WO02/054073

PCT Pub. Date: Jul. 11, 2002

(65) Prior Publication Data

US 2004/0146933 A1    Jul. 29, 2004

Related U.S. Application Data

(60) Provisional application No. 60/311,235, filed on Aug. 9, 2001, provisional application No. 60/260,348, filed on Jan. 8, 2001.

(51) Int. Cl.
| | |
|---|---|
| A61K 39/04 | (2006.01) |
| A61K 49/00 | (2006.01) |
| A61K 39/395 | (2006.01) |
| C12Q 1/00 | (2006.01) |
| C12N 5/00 | (2006.01) |
| C12N 5/08 | (2006.01) |

(52) U.S. Cl. ............ 424/248.1; 424/9.1; 424/9.2; 424/130.1; 424/139.1; 424/150.1; 424/184.1; 424/185.1; 424/234.1; 435/4; 435/325; 435/366; 435/372

(58) Field of Classification Search ........... 424/9.1, 424/9.2, 130.1, 139.1, 150.1, 184.1, 185.1, 424/234.1, 248.1; 435/4, 325, 366, 372
See application file for complete search history.

(56) References Cited

U.S. PATENT DOCUMENTS 5,700,925 A    12/1997  Bishai et al.

5,824,546 A    10/1998  Bishai et al.

FOREIGN PATENT DOCUMENTS

| WO | WO 97/26007 | 7/1997 |
| WO | WO 98/29132 | 7/1998 |
| WO | WO 99/02670 | 1/1999 |

OTHER PUBLICATIONS

Berengian et al., "Site-directed Spin Labeling Study of Subunit Interactions in the α-Crystallin Domain of Small Heat-Shock Proteins," *J. Biol. Chem.* 274(10):6305-6314, Mar. 1999.

Cunningham and Spreadbury, "Mycobacterial Stationary Phase Induced by Low Oxygen Tension: Cell Wall Thickening and Localization of the 16-Kilodalton α-Crystallin Homolog," *J. Bacteriol.* 180(4):801-808, Feb. 1998.

Dhandayuthapani et al., "Green fluorescent protein as a marker for gene expression and cell biology of mycobacterial interactions with macrophages," *Mol. Microbiol.* 17(5):901-912, Sep. 1995 (abstract only).

Garbe et al., "Response to Reactive Nitrogen Intermediates in *Mycobacterium tuberculosis*: Induction of the 16-Kilodalton α-Crystallin Homolog by Exposure to Nitric Oxide Donors," *Infect. Immun.* 67(1):460-465, Jan. 1999.

Hu and Coates, "Transcription of the Stationary-Phase-Associated *hspX* Gene of *Mycobacterium tuberculosis* Is Inversely Related to Synthesis of the 16-Kilodalton Protein," *J. Bacteriol.* 181(5):1380-1387, Mar. 1999.

Lalvani et al., "Enumeration of T Cells Specific for RD1-Encoded Antigens Suggests a High Prevalence of Latent *Mycobacterium tuberculosis* Infection in Healthy Urban Indians," *J. Infect. Dis.* 183:469-477, 2001.

Leiner and Mays, "Diagnosing Latent and Active Pulmonary Tuberculosis: A Review for Clinicians," *Nurse Practitioner* 21(2):86-111, Feb. 1996.

Manabe et al., "Conditional Sigma Factor Expression, Using the Inducible Acetamidase Promoter, Reveals the the *Mycobacterium tuberculosis sigF* Gene Modulates Expression of the 16-Kilodalton Alpha-Crystallin Homologue," *J. Bacteriol* 181(24):7629-7633, Dec. 1999.

(Continued)

*Primary Examiner*—Rodney P Swartz
(74) *Attorney, Agent, or Firm*—Klarquist Sparkman, LLP

(57) ABSTRACT

Provided herein is an in vitro granuloma model and methods of its use. Methods of detecting and/or diagnosing latent tuberculosis in a subject are also provided, as are latency-specific antigens (and antibodies thereto), such as α-crystallin, and methods of identifying and using such molecules. Also provided are immunostimulatory compositions, for instance for use in eliciting an immune response in a subject, such as an immune response to a latent tuberculosis infection. Kits for carrying out the provided methods are also described.

27 Claims, 7 Drawing Sheets

OTHER PUBLICATIONS

Mehrotra et al., "Antigenic definition of plasma membrane proteins of Bacillus Calmette-Guerin: predominant activation of human T cells by low-molecular-mass integral proteins," *Scand. J. Immunol.* 50(4):411-419, Oct. 1999 (abstract only).

Monahan et al., "Differential expression of mycobacterial proteins following phagocytosis by macrophages," *Microbiol.* 147(Pt. 2):459-471, Feb. 2001.

Verbon et al., "The 14,000-molecular-weight antigen of *Mycobacterium tuberculosis* is related to the alpha-crystallin family of low-molecular-weight heat shock proteins," *J. Bacteriol.* 174(4):1352-1359, Feb. 1992 (abstract only).

Wayne and Hayes, "An In Vitro Model for Sequential Study of Shiftdown of *Mycobacterium tuberculosis* through Two Stages of Nonreplicating Persistance," *Infect. Immunit.* 64(6):2062-2069, Jun. 1996.

Wilkinson et al., "Human T- and B-Cell Reactivity to the 16 kDa α-Crystallin Protein of *Mycobacterium tuberculosis,*" *Scand. J. Immunol.* 48(4):403-409, Oct. 1998.

Yang et al., "The *Mycobacterium tuberculosis* small heat shock protein Hsp16.3 exposes hydrophobic surfaces at mild conditions: conformational flexibility and molecular chaperone activity," *Protein Sci.* 8(1):174-179, Jan. 1999 (abstract only).

Yuan et al., "Stationary Phase-Associated Protein Expression in *Mycobacterium tuberculosis*: Function of the Mycobacterial α-Crystallin Homolog," *J. Bacteriol.* 178(15):4484-4492, Aug. 1996.

Yuan et al., "16-kDa α-crystallin (Acr) protein of *Mycobacterium tuberculosis* is required for growth in macrophages," *Proc. Natl. Acad. Sci. USA* 95(16):9578-9583, Aug. 1998.

http://www.gen-probe.com/mtd.html, "AMPLIFIED™ Mycobacterium Tuberculosis Direct Test," May 15, 2001 (16 pages).

http://www.ima.umn.edu/biology/wkshp_abstracts/jacobsonl.html, Jacobson, "Multi-Analyte Profiling with Suspension Arrays™," May 15, 2001 (1 page).

http://www.luminexcorp.com/products/devcalsphere.htm, "Development Microspheres," May 15, 2001 (3 pages).

http://www.luminexcorp.com/tech/, "LabMAP: Laboratory Multiple Analyte Profiling," May 15, 2001 (2 pages).

http://www.wiley.com/products/subject/life/cytometry/ISAC98/5MAEChan.htm, Chandler et al., "Biomolecular multiplexing of up to 512 assays on a new solid-state, 4 color flow analyzer," May 15, 2001 (1 page).

1 2 3 4 5 6

LATENT HUMAN TUBERCULOSIS MODEL, DIAGNOSTIC ANTIGENS, AND METHODS OF USE

This is the U.S. National Stage of International Application No. PCT/US02/00309, filed Jan. 7, 2002, which was published in English under PCT Article 21(2), which in turn claims the benefit of U.S. Provisional Application No. 60/260,348, filed Jan. 8, 2001 and U.S. Provisional Application No. 60/311,235, filed Aug. 9, 2001. All three applications are incorporated herein in their entirety.

STATEMENT OF GOVERNMENT SUPPORT

This invention was made by the Centers for Disease Control and Prevention, an agency of the United States Government. Therefore, the U.S. Government has certain rights in this invention.

FIELD OF THE DISCLOSURE

The present disclosure relates to the field of mycobacterial latency, and in particular relates to an in vitro granuloma model for the study of mycobacteria and for the development of tuberculosis drug and vaccine candidates, and to the detection of latent mycobacterial infection using immunoassays.

BACKGROUND

Approximately every ten seconds, a person dies of tuberculosis somewhere in the world. Tuberculosis is the world's number one killer among infectious diseases and the leading cause of death among women of reproductive age. Although developing countries bear the greatest burden of disease, the United States is greatly affected by tuberculosis, reporting 16,377 cases in 2000.

The infectious agent causing almost all cases of tuberculosis is *Mycobacterium tuberculosis* (*M. tuberculosis*). *M. tuberculosis* is easily spread between individuals through the air. A single cough by an infected individual can generate as many as 3000 infected droplet nuclei, while less than 10 bacilli may initiate a pulmonary infection in a susceptible individual. Because simply inhaling an airborne pathogen may infect individuals, tuberculosis outbreaks are difficult to contain and require isolating the infected individuals in negative air pressure rooms.

Although it was believed that tuberculosis would eventually be eliminated after the development of antibiotics in the 1950s, in 1999, tuberculosis was labeled as a global health emergency by the World Health Organization. One of the major reasons for the perseverance of tuberculosis is the evolution of multi-drug resistant strains. Multi-drug resistant strains have evolved in part due to infected patients' poor compliance with drug therapy, which lasts for a period of at least six months. One multi-drug resistant strain, strain W, has evolved resistance to all first-line drugs (isoniazid, rifampin, ethambutol, and pyrazidine), as well as one second-line drug (kanamycin). It is therefore evident that tuberculosis continues to be a serious health threat to individuals worldwide.

Initial infection with *M. tuberculosis* only rarely leads to immediate disease because the infection is typically controlled by the host's immune system. Among people infected with *M. tuberculosis*, approximately 5% manifest the disease within a few years after infection. Upon initial infection, the mycobacteria enter unactivated macrophages and multiply therein. Following a rapid growth phase, infected macrophages and their bacilliary cargo are surrounded and walled off by newly recruited activated macrophages. This walling off of the infected macrophages results in the characteristic granuloma. The granuloma is a compact, organized collection of activated macrophages, including epithelioid and multinucleated giant cells; surrounded by T lymphocytes, and later by fibroblasts and collagen, which aggregate around the macrophage core.

Mycobacterial dormancy results in a disease stage termed latent tuberculosis. An individual with latent tuberculosis may later develop a case of reactivated tuberculosis, and in fact, the majority of the tuberculosis cases reported in the United States are the result of reactivation of a mycobacterial infection and not an initial infection. (*Am. Rev. Respir. Dis.* 146:1623–1633, 1992). Reactivation of the *M. tuberculosis* bacilli usually occurs in the apex of the lung where large numbers of tubercle bacilli cause necrosis of the small bronchi of the lung. The characteristic bloodstained sputum of tuberculosis results from the erosion of small blood vessels during this necrotic process.

Approximately one-third of the population worldwide has been estimated to be latently infected with *M. tuberculosis*. (Sudre et al., *Bull. W.H.O.* 70:149–159, 1992). Currently, the tuberculin skin test is the only available diagnostic for those infected with *M. tuberculosis*. Unfortunately, no currently available test can specifically identify latently infected individuals. The tuberculin test is only capable of identifying all individuals either exposed to the pathogen or vaccinated against the pathogen. Due to the high number of latently infected individuals and the risk of reactivation of tuberculosis in those individuals, diagnostics and therapeutics targeted to latent tuberculosis need to be developed. In addition, the development of an in vitro granuloma model for the study of mycobacteria and for the development of tuberculosis drug and vaccine candidates would be desirable.

SUMMARY OF THE DISCLOSURE

An in vitro model for tuberculosis latency is described in certain embodiments of this disclosure. In particular, an in vitro granuloma model and methods for using the model are provided. In some embodiments, the in vitro granuloma model contains human peripheral blood mononuclear cells, autologous macrophages and mycobacteria. In some embodiments these components are combined in a low-attachment container. In specific examples, the in vitro granuloma model further contains fibroblasts, for example, human lung fibroblasts.

Further embodiments are methods for using the in vitro granuloma model to screen new or known compounds for their effects on granuloma, for instance to screen candidate tuberculosis drugs, to identify candidate tuberculosis vaccines, and to analyze and characterize the process of granuloma formation and granuloma necrosis.

Also provided herein are immunological methods for detecting latent tuberculosis infections. Such methods are based on detecting specific bacterial antigens (or antibodies against these antigens) that are present in a subject with tuberculosis only (or predominately) during latent infection. By way of example, one such latency-specific antigen is alpha-crystallin (Acr).

Further embodiments include an immunological assay for detection of latent tuberculosis in a subject, which assay involves contacting a biological sample from the subject, wherein the sample is suspected of containing a first latency-specific biding partner (LSBP) (such as a latency-specific antigen or an antibody thereto), with a second (corresponding) LSBP, and detecting binding between the first LSBP and the corresponding LSBP. Binding between the first and second LSBPs is indicative of latent tuberculosis in the subject. Thus, in one example where the first LSBP is a *M. tuberculosis* latency-specific antigen (for instance, Acr or an immunogenic fragment thereof), the corresponding LSBP may be an antibody that is capable of binding to that antigen. Where the first LSBP is an antibody, the corresponding LSBP (to make a specific binding pair) is an antigen.

Also provided are kits for the detection of latent tuberculosis in a subject, which kits include at least one LSBP (e.g., a latency-specific antigen or antibody thereto) and instructions for carrying out an immunological assay to detect binding of the LSBP to a cognate LSBP found in a biological sample.

Also provided are kits comprising one or more elements of an in vitro granuloma model, for instance cell culture media and, optionally, low-attachment containers and/or instructions for growing in vitro granulomas.

Further embodiments provide methods for eliciting an immune response in a subject by administering to the subject an immune stimulatory amount of a *M. tuberculosis* latency-specific antigen (e.g., Acr), or immunogenic fragment thereof. Compositions containing such immunostimulatory molecules, and kits for their administration, are also provided.

The foregoing and other features and advantages will become more apparent from the following detailed description of several embodiments, which proceeds with reference to the accompanying figures and sequence listing.

BRIEF DESCRIPTION OF THE FIGURES

FIG. 1A shows tissue that was stained with hematoxylin and eosin (H & E). FIG. 1B shows tissue that was stained with acid-fast stain; representative mycobacterium are indicated by the arrows. FIG. 1C shows tissue that was subjected to immunohistochemical staining using a polyclonal antibody against the Acr protein; the arrows indicate two stained mycobacteria.

Key: Lane 1, Uninfected Guinea Pig Lung; lane 2, MTB-Infected Guinea Pig Lung—3 weeks P.I; lane 3, MTB-Infected Guinea Pig Lung—5 weeks P.I.; lane 4, MTB-Infected Guinea Pig Lung—10 weeks P.I.; lane 5, MTB-7 Day Anoxic Culture.

Figure 5:
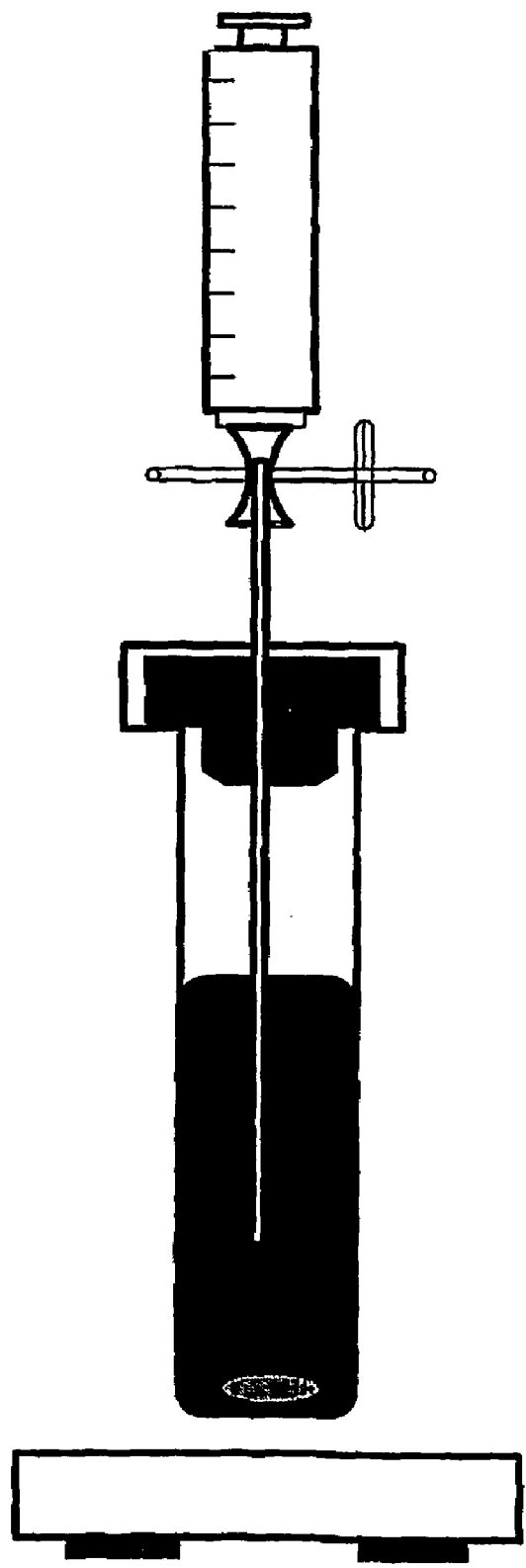

FIG. 5 is a schematic drawing of an example anoxic growth vessel.

Figure 6:
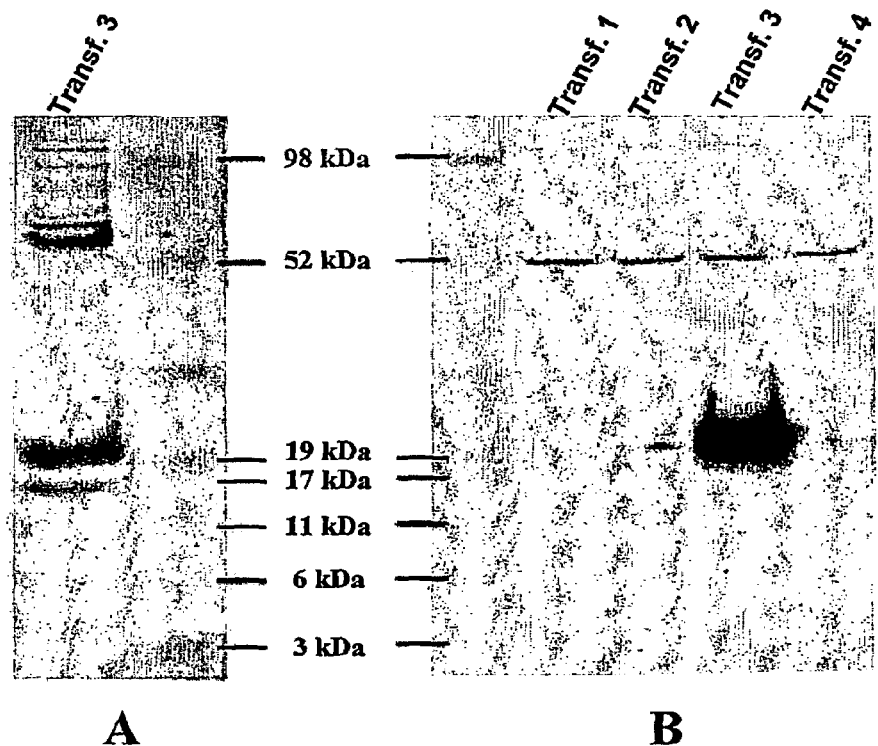

FIG. 6 is a pair of Western blots demonstrating the production of the N-terminal construct Acr-N-FLAG in transformant 3. The blot in FIG. 6A was probed with anti-Acr polyclonal immunoglobin. The blot in FIG. 6B was probed with anti-FLAG epitope immunoglobin.

Figure 7:
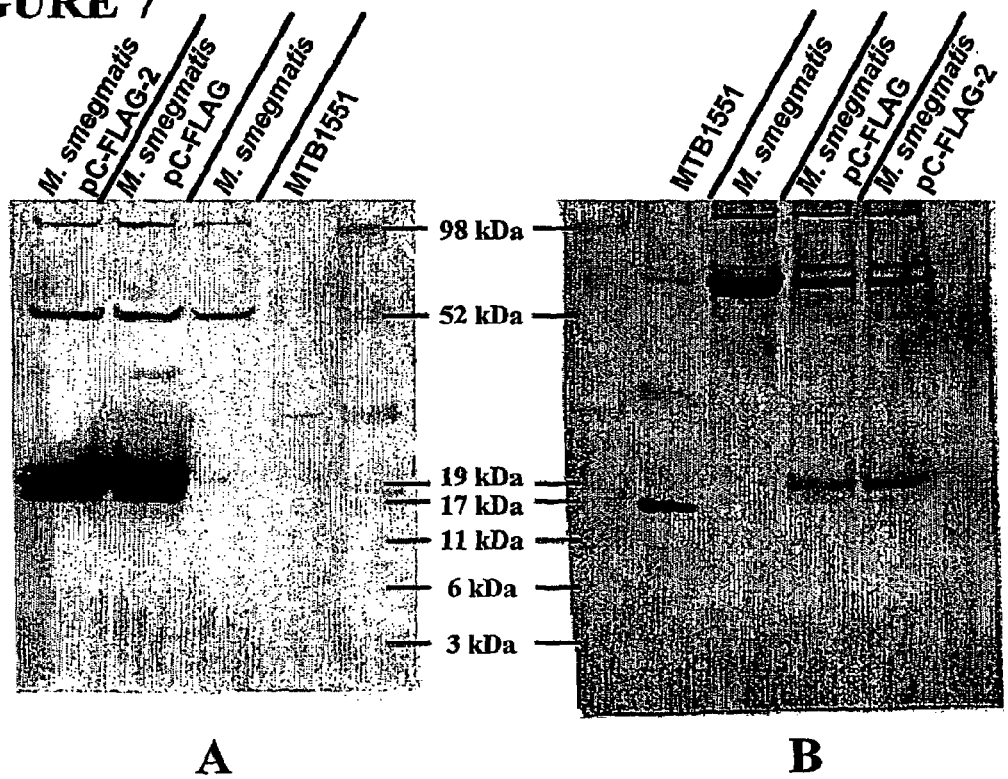

FIG. 7 is a pair of Western blots of whole cell lysates demonstrating the production of the C-terminal construct Acr-C-FLAG in two *Myobacterium smegmatis* transformed strains versus non-transformed *M. smegmatis* and *M. tuberculosis* controls. The blot in FIG. 7A was probed with anti-FLAG immunoglobin. The blot in FIG. 7B was probed with anti-Acr immunoglobin.

Figure 8:
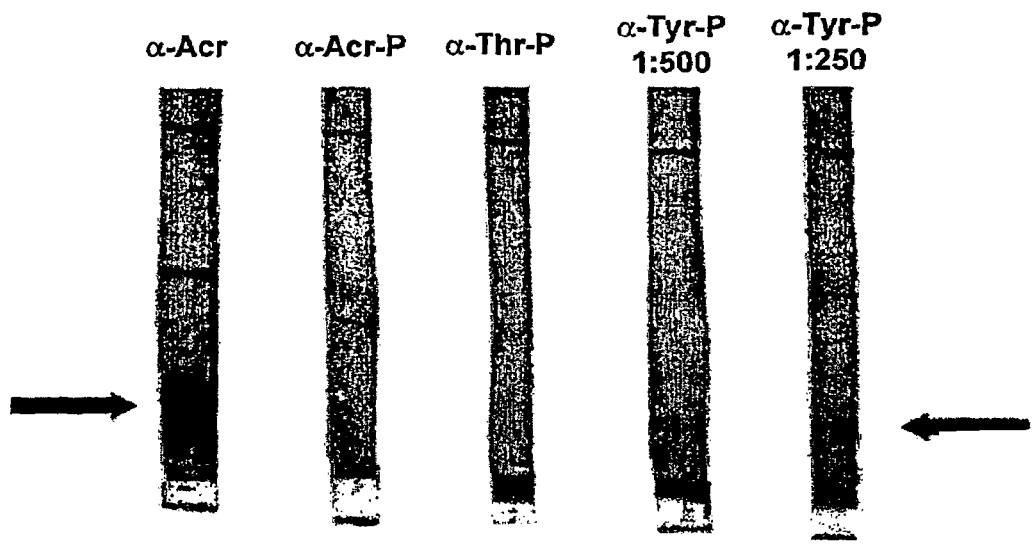

FIG. 8 shows five strips cut from a Western blot of whole cell lysates; the arrows indicate the location of recombinant Acr protein. The strips were developed with the indicated primary antibodies. In addition to the control antibody, this blot demonstrates the presence of tyrosine phosphorylation in the final strip.

Figure 9:
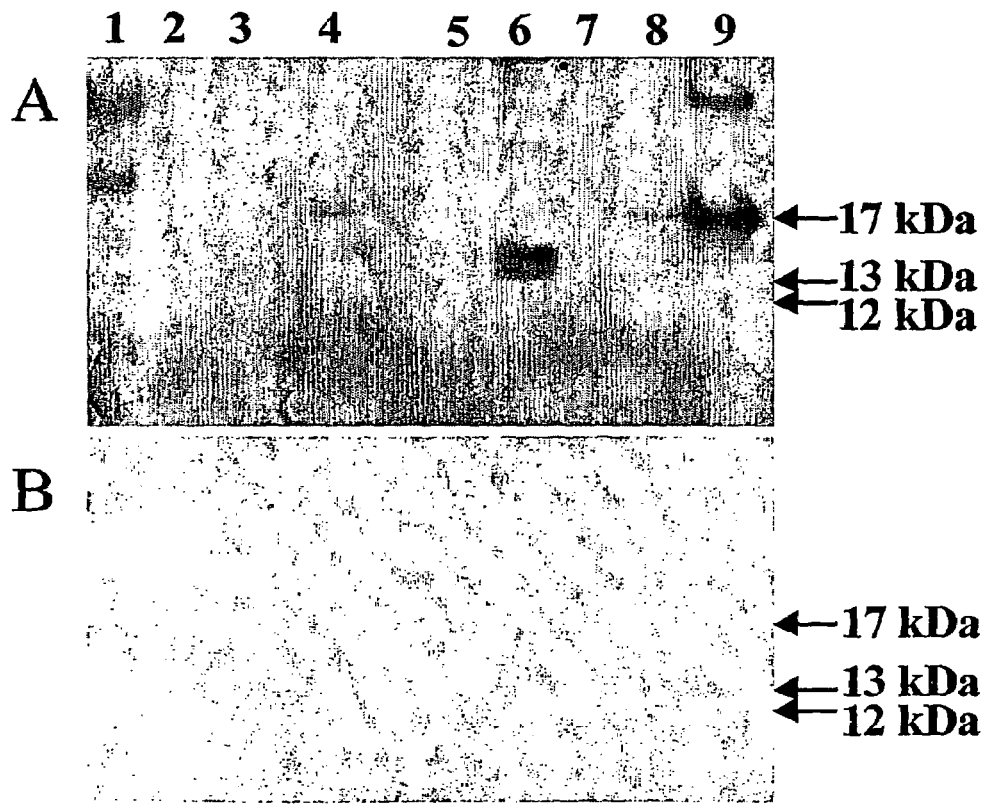

FIG. 9 shows two Western blots from culture supernatants of *M. tuberculosis* bacilli grown under various conditions. FIG. 9A was probed using rabbit anti-Acr antibody; FIG. 9B is a control blot. Protein is detected in 7 day and 12 month anoxic cultures and in vitro granuloma. Lower molecular weight variants are observed in the 12-month and in vitro granuloma supernatants.

Key: Lane 1, molecular weight marker; lane 2, 3 day aerobic growth; lane 3, 7 day aerobic growth; lane 4, 7 day anoxic growth; lane 5, blank; lane 6, 7 day react; lane 7, 12 months react; lane 8, control cells; lane 9, 7 day in vitro granulomas; lane 10, *M. tuberculosis* lysate.

Figure 10:
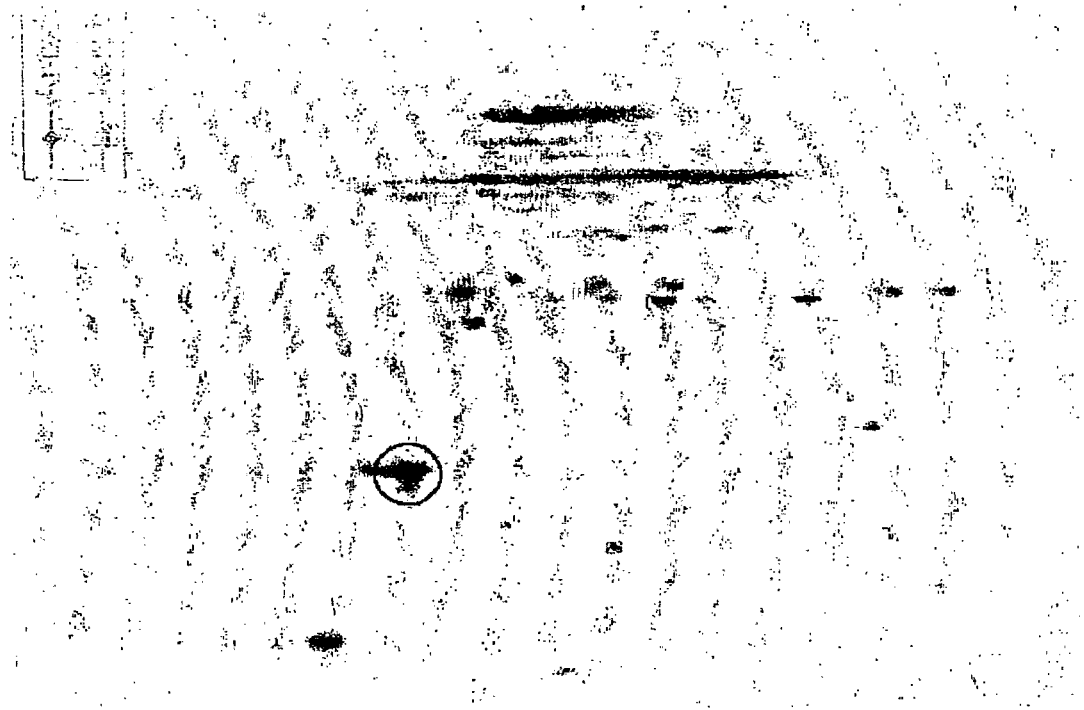

FIG. 10 is a two-dimensional gel electrophoresis analysis of a sample taken from *M. tuberculosis* grown under anoxic conditions. Acr protein is indicated by the circle.

Figure 11:
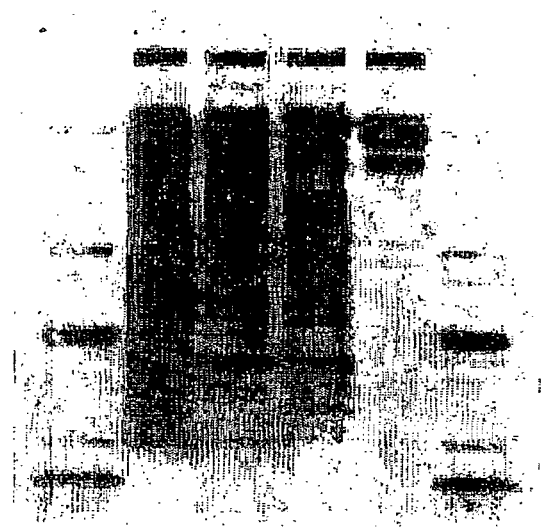

FIG. 11 is a Coomassie stained SDS-PAGE gel of culture supernatants from *M. tuberculosis* bacilli cultured under a variety of conditions.

Key: Lane 1, MW marker, lane 2, 5-day aerobic (logarithmic); lane 3, anoxic 12 months; lane 4, anoxic 7 days; lane 5, 30-hour aerobic reactivated (logarithmic); lane 6, MW marker.

Figure 12:
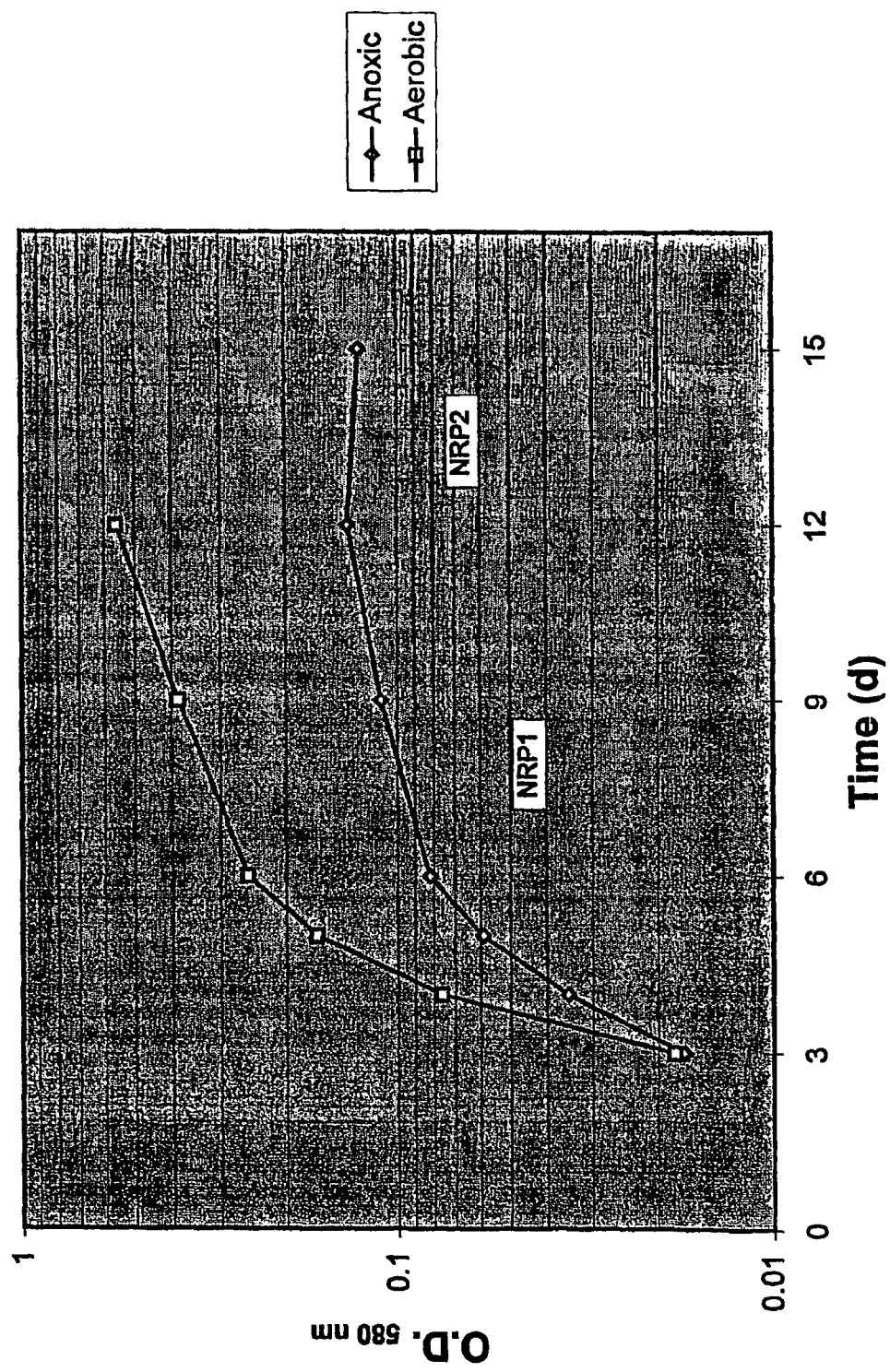

FIG. 12 is a graph showing the growth (measured by optical density at 580 nm) of *M. tuberculosis* under anoxic and aerobic growth conditions.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1 and 2 are the sequences of primers used to generate the N-terminal FLAG-Acr fusion.

SEQ ID NOs: 3 and 4 are the sequences of primers used to generate the C-terminal Acr-FLAG fusion.

DETAILED DESCRIPTION

I. Abbreviations

| Acr | alpha (α) crystallin |
| ELISA | enzyme-linked immunosorbent assay |

-continued

| | |
|---|---|
| HS | human serum |
| LSA | latency-specific antigen |
| LSBP | latency-specific binding partner |
| PBMCs | peripheral blood mononuclear cells |
| RPA | ribonuclease protection assay |
| RT-PCR | reverse-transcription polymerase chain reaction |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

The terms "a," "an," and "the" as used herein are defined to mean one or more and include the plural unless the context is inappropriate.

The term "antibody" refers to a protein (or protein complex) that includes of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term antibodies includes intact immunoglobulins as well as a number of well-characterized fragments produced by digestion with various peptidases, or genetically engineered "artificial" antibodies. Thus, for example, pepsin digests an antibody below the disulfide linkages in the hinge region to produce F(ab)'$_2$, a dimer of Fab which itself is a light chain joined to $V_H$—$C_H$ 1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially a Fab with part of the hinge region (see, *Fundamental Immunology*, W., E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495–497, 1975) or derivative methods thereof. Detailed procedures for monoclonal antibody production are described in Harlow and Lane (*Antibodies, A Laboratory Manual*, CSHL, New York, 1988).

The term "antigen" refers to a molecule, or fragment thereof, which can induce an immune response in a mammal. The term includes immunogens and regions responsible for antigenicity or antigenic determinants. A chemical or biochemical structure, determinant, antigen or portion thereof that is capable of inducing the formation of an antibody can be referred to as being "antigenic." "Antigenic determinant" refers to a region of a specified protein that is recognized by an antibody.

When referring to macrophages, the term "autologous" refers to macrophages that are derived from the same individual as the peripheral blood mononuclear cells. Alternatively, a macrophage cell line such as, but not limited to the THP-1 macrophage cell line is used as the macrophage component of the granuloma model. In one embodiment of the present disclosure, the beginning concentration of the autologous macrophages is between approximately $5 \times 10^4$ and $1 \times 10^6$, per two-milliliter sample, and optionally at a beginning concentration of approximately $1 \times 10^6$.

A "biological sample" is a sample of bodily fluid or tissue used for laboratory testing or examination. As used herein, biological samples include all clinical samples useful for detection of microbial infection in subjects.

Tissue samples may be taken from the oropharyngeal tract, for instance from lung or bronchial tissue. Samples can be taken by biopsy (such as during a bronchoscopy) or during autopsy examination, as appropriate. Biological fluids include blood, derivatives, and fractions of blood such as serum, urine, semen and fluids of the oropharyngeal tract, such as sputum.

Examples of specimens for use with the current disclosure for the detection of latent *M. tuberculosis* include conventional clinical samples, for instance blood or blood-fractions (e.g., serum), urine, bronchoalveolar lavage (BAL), sputum, and induced sputum samples. Techniques for acquisition of such samples are well known in the art. Blood and blood fractions can be prepared in traditional ways. Oropharyngeal tract fluids can be acquired through conventional techniques, including sputum induction, bronchoalveolar lavage (BAL), and oral washing. Obtaining a sample form oral washing involves having the subject gargle with an amount normal saline for about 10–30 seconds and then expectorate the wash into a sample cup.

The "condition" or "conditions" under which a DNA strand is synthesized include the presence of nucleotides, cations, and appropriate buffering agents in amounts and at temperatures such that the nucleic acid molecule and a DNA primer will anneal and oligonucleotides will be incorporated into a synthesized DNA strand.

As used herein, the terms "detecting" or "detection" refers to quantitatively or qualitatively determining the presence of a biomolecule under investigation.

"Epitope tags" are short stretches of amino acids to which a specific antibody can be raised, which in some embodiments allow one to specifically identify and track a protein tagged with the epitope. Detection of the tagged molecule can be achieved using a number of different techniques. Examples of such techniques include: immunohistochemistry, immunoprecipitation, flow cytometry, immunofluorescence microscopy, ELISA, immunoblotting ("western"), and affinity chromatography. Examples of epitope tags include FLAG, T7, HA (hemagglutinin) and myc.

As used herein, the term "granuloma" refers to a compact, organized collection of activated macrophages, including epithelioid and multinucleated giant cells, surrounded by *T lymphocytes,* fibroblasts and collagen. It is to be understood, however, that the term "in vitro granuloma" is not limited to a collection of cells as described above. The term "in vitro granuloma" refers to a collection or aggregate of cells containing at least human peripheral blood mononuclear cells and autologous macrophages, wherein the collection or aggregate of cells mimics the granuloma as described above. Whether the in vitro granuloma mimics the granuloma as described above, and as found in vivo, is determined by methods known to those skilled in the art, such as microscopic examination of the cell aggregates, phenotypic analysis of cells within the aggregates, via FACS (fluorescence activated cell sorter) analysis for example, and analysis of cytokine production by the cells within the aggregates.

As used herein, the term "human peripheral blood mononuclear cells" (PBMCs) includes, but is not limited to, *monocytes, B lymphocytes,* and *T lymphocytes.* The human PBMCs included in examples of the in vitro granuloma model can be monocytes and *T lymphocytes.* Optionally, in certain embodiments the in vitro granuloma model contains monocytes at a beginning concentration of between approximately $5\times10^4$ and $1\times10^6$, per two milliliter sample, and *T lymphocytes* at a beginning concentration of between approximately $1\times10^5$ and $1\times10^6$. In some embodiments, the in vitro granuloma model contains monocytes at a beginning concentration of approximately $1\times10^6$ and *T lymphocytes* at a beginning concentration of approximately $1\times10^6$. It is to be understood that the term "beginning concentration" refers to the concentration of material as it is added to a low attachment container.

In some embodiments, the In vitro granuloma model contains fibroblasts, such as human lung fibroblasts. Optionally, the fibroblasts can be added at a beginning concentration of between approximately $1\times10^5$ and $1\times10^6$, for instance, at a beginning concentration of approximately $5\times10^5$.

A "low attachment container" is a container whose surface inhibits or reduces the attachment of cells in culture. In some embodiments, the low attachment container is a low attachment tissue culture dish such as, but not limited to, the COSTAR™ Ultra Low Attachment Surface or Clusters (Costar Corp., Cambridge, Mass.) used in accordance with the manufacturer's recommended procedures. Optionally, the low attachment container can have a surface composed of a covalently bound hydrogel layer that is hydrophilic and neutrally charged, so that it inhibits (for instance, by 5%, 10%, 20%, 40%, 50% or more compared to a non-coded container) the attachment and activation of macrophages and neutrophils. Because proteins and other biomolecules passively adsorb to surfaces through hydrophobic and ionic interactions, a hydrogel surface naturally inhibits non-specific immobilization via these forces, thus inhibiting subsequent cell attachment. Optionally, the surface of the low attachment container may be rehydrated at a temperature consistent with the application or cell growth requirements of the cells described above and the rehydration media aspirated or decanted prior to the addition of cells and fresh media. Alternatively, the cells may be added directly to the rehydration media "In vitro amplification" refers to techniques that increase the number of copies of a nucleic acid molecule in a sample or specimen. An example of in vitro amplification is the polymerase chain reaction (PCR), in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify copies of the nucleic acid. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filing ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134). The product of in vitro amplification may be characterized by electrophoresis, restriction endonuclease cleavage patterns, oligonucleotide hybridization or ligation, and/or nucleic acid sequencing, using standard techniques.

An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and/or organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids. As with the term purified, isolated is a relative term.

A "label" is any molecule or composition that is detectable by, for instance, spectroscopic, photochemical, biochemical, immunochemical, electrical, optical, or chemical means. Examples of labels, including radioactive isotopes, enzyme substrates, co-factors, ligands, chemiluminescent or fluorescent agents, haptens, enzymes, colloidal gold particles, colored latex particles, and epitope tags, have been disclosed previously and are known to those of ordinary skill (see, for instance, U.S. Pat. Nos. 4,275,149; 4,313,734; 4,373,932; and 4,954,452).

The attachment of a compound (e.g., an antibody) to a label can be through covalent bonds, adsorption processes, hydrophobic and/or electrostatic bonds, as in chelates and the like, or combinations of these bonds and interactions and/or may involve a linking group.

"Latent tuberculosis" refers to a stage in the *M. tuberculosis* infection where the bacilli remain viable but are slowly replicating or non-replicating, may be encapsulated in localized lesions within the lung, and do not cause active necrotic disease. The latent stage may exist for the remainder of a host's life, or the infection may reactivate during, for instance, a period of decreased host immunity or in response to other stressors. Though latent *M. tuberculosis* infections have not previously been able to be specifically identified, they are within the group of individuals that possess a positive tuberculin skin test but do not possess the characteristic symptoms of active disease.

A "latency specific antigen" is an antigen that is expressed at higher levels (or exclusively) by a *M. tuberculosis* bacterium in its dormant or stationary rather than its active or logarithmic phase of growth. Latency specific antigens (LSAs) can be identified, for instance, by comparing the protein expression found in in vitro cultured *M. tuberculosis* grown under standard aerobic/logarithmic conditions with bacilli grown under conditions that mimic latency (e.g., in a latency model).

A "linking group" is a chemical arm between two compounds, for instance a compound and a label (e.g., an antibody and a label). To accomplish the requisite chemical structure of the linkage, each of the reactants must contain a reactive group. Representative combinations of such groups are amino with carboxyl to form amide linkages; carboxy with hydroxy to form ester linkages; amino with alkyl halides to form alkylamino linkages; thiols with thiols to form disulfides; or thiols with maleimides or alkylhalides to form thioethers. Hydroxyl, carboxylamino and other functionalities, where not present in the native compound, may be introduced by known methods.

Likewise, a wide variety of liking groups may be employed. The structure of the linkage should be a stable covalent linkage formed to attach two compounds to each other (e.g., the label to the antibody). In some cases the linking group may be designed to be either hydrophilic or hydrophobic in order to enhance a desired characteristic, for instance a binding characteristic of a modified ligand and its cognate receptor. The covalent linkages should be stable relative to the solution conditions to which linked compounds are subjected.

Examples of linking groups will be from 1–20 carbons and 0–10 heteroatoms (NH, O, S) and may be branched or straight chain. Without limiting the foregoing, it should be obvious that only combinations of atoms that are chemically compatible comprise the lining group. For example, amide, ester, thioether, thiol ester, keto, hydroxylcarboxyl, and ether groups in combinations with carbon-carbon bonds are particular examples of chemically compatible linking groups.

The term "mycobacteria" as used herein includes, but is not limited to, *M. tuberculosis*. Any mycobacteria that form granulomas can be used in the compositions and methods provided herein. Exemplary mycobacteria include *M. avium, M. bovis, M. marinum, M. ulcerans, M. smegmatis*, and *M. haemophilum*. Optionally, the beginning concentration of mycobacteria in the in vitro granuloma model is between approximately $1 \times 10^1$ and $1 \times 10^5$ cfu/2 ml sample.

A first nucleic acid sequence is "operably linked" with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably lined DNA sequences are contiguous and, where necessary to join two protein-coding regions, in the same reading frame.

"Peptides," "polypeptides," and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal end of the peptide, or to the alpha-amino group (imino group when participating in a peptide bond) of an amino acid at any other location within the peptide. The term "carboxy terminus" (abbreviated C-terminus) refers to the free carboxyl group on the amino acid at the carboxy terminal end of a peptide, or to the carboxyl group of an amino acid at any other location within the peptide.

Typically, the amino acids making up a peptide are numbered in order, starting at the amino terminus and increasing in the direction toward the carboxy terminus of the peptide. Thus, when one amino acid is said to "follow" another, that amino acid is positioned closer to the carboxy terminal end of the peptide than the preceding amino acid.

As used herein, the term "primer" or "DNA primer" means an oligonucleotide that anneals to a nucleic acid molecule in a particular orientation to allow for the synthesis of a nascent DNA strand.

As used herein, the phrase "primer pair" refers to two primers, one having a forward designation and the other having a reverse designation (relative to their respective orientations when annealed to a double-stranded DNA molecule that consists of a sense and antisense sequence). Under in vitro amplification conditions, the forward primer anneals to and primes amplification of the sense sequence and the reverse primer anneals to and primes amplification of the antisense sequence. Primers can be selected for use in an amplification reaction on the basis, for instance, of having minimal complementarity with other primers in the reaction (to minimize the formation of primer dimers) and having $T_m$ values with a range of reaction temperatures appropriate for the amplification method, such as PCR. In addition, primers can be selected to anneal with specific regions of a DNA or RNA template such that the resulting DNA amplification product of specific size, for instance from 100 to 5000 base pairs in length, for instance around 300 base pairs in length or longer.

By "probe" is meant a nucleic acid sequence that can be used for selective hybridization with complementary nucleic acid sequences for their detection. The probe varies in length, for instance from about 5 to 100 nucleotides, or from about 10 to 50 nucleotides, or about 18 to 24 nucleotides. A "labeled probe" comprises an isolated nucleic acid probe attached to a detectable label or other reporter molecule. Methods for labeling and guidance in the choice of labels appropriate for various purposes are discussed, e.g., in Sambrook et. al. (In *Molecular Cloning: A Laboratory Manual*, CSHL, New York, 1989) and Ausubel et al. (In *Current Protocols in Molecular Biology*, John Wiley & Sons, New York, 1998).

A "promoter" includes one or more nucleic acid sequences that direct transcription of a nucleic acid. A promoter includes nucleic acid sequences near the start site of transcription, such as, in the case of a polymerase II type promoter, a TATA element. A promoter may also include distal enhancer or repressor elements that can be located as much as several thousand base pairs from the start site of transcription.

The term "purified" as it is used herein does not require absolute purity; rather, it is intended as a relative term. Thus, for example, a purified nucleic acid (or protein or other compound) preparation is one in which the specified molecule (or type of molecule) is more enriched than it is in its generative environment, for instance within a cell or in a biochemical reaction chamber (as appropriate). A preparation of a "substantially pure" substance, for instance a substantially pure nucleic acid, may be purified such that the desired nucleic acid represents at least 50% of the total nucleic acid content of the preparation. In certain embodiments, a substantially pure preparation will represent at least 60%, at least 70%, at least 80%, at least 85%, at least 90%, or at least 95% or more desired molecule in the preparation.

A "recombinant" nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

The term "residue" is used herein to refer to an amino acid (D or L), or an amino acid mimetic, that is incorporated into a peptide by an amide bond. As such, the amino acid may be a naturally occurring amino acid or, unless otherwise limited, may encompass analogs of natural amino acids that function in a manner similar to the naturally occurring amino acids (i.e., amino acid mimetics). Moreover, an amide bond mimetic includes peptide backbone modifications well known to those of ordinary skill in the art.

The phrase "sequence identity" refers to the similarity between two nucleic acid sequences, or two amino acid sequences, and is expressed in terms of the similarity between the sequences. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman *Adv. Appt Math.* 2: 482, 1981; Needleman & Wunsch *J. Mol. Biol.* 48:443, 1970; Pearson & Lipman *Proc. Natl. Acad. Sci. USA* 85: 2444, 1988; Higgins & Sharp *Gene,* 73: 237–244, 1988; Higgins & Sharp *CABIOS* 5: 151–153, 1989; Corpet et al. *Nuc. Acids Res.* 16, 10881–90, 1988; Huang et al. *Computer Appls. in the Biosciences* 8, 155–65, 1992; and Pearson et al. *Meth. Mol. Bio.* 24, 307–31, 1994. Altschul et al. (*J. Mol. Biol.* 215:403–410, 1990), presents a detailed consideration of sequence alignment methods and homology calculations.

The NCBI Basic Local Alignment Search Tool (BLAST) (Altschul et al., *J. Mol. Biol.* 215:403–410, 1990) is available from several sources, including the National Center for Biotechnology Information (NCBI, Bethesda, Md.) and on the Internet, for use in connection with the sequence analysis programs blastp, blastn, blastx, tblastn and tblastx.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al (In *Molecular Cloning: A Laboratory Manual*, CSHL, New York, 1989) and Tijssen (*Laboratory Techniques in Biochemistry and Molecular Biology*—Hybridization with Nucleic Acid Probes Part I, Chapter 2, Elsevier, New York, 1993). Nucleic acid molecules that hybridize under stringent conditions to a target sequence will typically hybridize to a probe based on either an entire target protein encoding sequence, or selected portions of the encoding sequence, under wash conditions of 2×SSC at 50° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein or the identical protein.

Furthermore, one of ordinary skill in the art will recognize that individual substitutions, deletions or additions in the amino acid sequence of the protein, or in the nucleotide sequence encoding for the amino acids in the protein, which alter, add or delete a single amino acid or a small percentage of amino acids (in some instances less than 5%, or even less than 1%) in an encoded sequence are conservatively modified variations, wherein the alterations result in the substitution of an amino acid with a chemically similar amino acid, and so long as the resultant variant still retains a substantial proportion of a property or activity, such as an immunostimulatory property (e.g., a protective immune response in a subject), of the base protein. Envisioned in specific embodiments are molecules in which there is no more than one amino acid substitution, no more than about three substitutions, or about 5, 10, or even 20 substitutions, so long as the resultant variant retains a substantial proportion (e.g., at least 20%, at least 30%, at least 50%, at least 75%, at least 80%, at least 90%, at least 95%, at least 98%, or more) of an immunostimulatory or other property of the base protein. Some variant embodiments are expected to have greater immunostimulatory properties than the protein or peptide from which they are derived.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "specific binding agent" as used herein refers to an agent that binds substantially only to a defined target. Thus a protein-specific binding agent binds substantially only the specified protein. The term "protein specific binding agent" includes anti-protein antibodies (and functional fragments thereof) and other agents (such as soluble receptors) that bind substantially only to the specified protein.

Anti-protein antibodies (such as anti-Acr antibodies) may be produced using standard procedures described in a number of texts, including Harlow and Lane (*Antibodies, A Laboratory Manual*, CSHL, New York, 1988). The determination that a particular agent binds substantially only to the specified protein, or component epitopes thereof may readily be made by using or adapting routine procedures. One suitable in vitro assay makes use of the Western blotting procedure (described in many standard texts, including Harlow and Lane (Antibodies, A Laboratory Manual, CSHL, New York, 1988)). Western blotting may be used to determine that a given protein binding agent, such as an anti-Acr monoclonal antibody, binds substantially only to the specified protein.

Shorter fragments of antibodies can also serve as specific binding agents. For instance, Fabs, Fvs, and single-chain Fvs (SCFvs) that bind to Acr would be Acr-specific binding agents. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2)

Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

A "specific binding partner" is a member of a pair of molecules (the "specific binding pair") capable of recognizing and binding to a structural aspect of another molecule by means of specific, noncovalent interactions that depend on the three-dimensional structures of the molecules involved. Typical pairs of specific binding partners include antigen/antibody, hapten/antibody, hormone/receptor, nucleic acid strand/complementary nucleic acid strand, substrate/enzyme, inhibitor/enzyme, apoprotein/cofactor, carbohydrate/lectin, biotin/(strept)avidin, and virus/cellular receptor.

A specific binding pair that includes at least one immunological molecule (such as an antibody or antigen) can be referred to as a specific immunological binding pair, and the immunological molecule(s) as specific immunological binding partner(s).

An example of a specific binding pair is a latency-specific binding pair, which includes a molecule that is a latency-specific molecule (such as a latency-specific antigen) and a molecule that is a specific binding partner for that latency-specific molecule.

The phrase "specifically binds to an analyte" or "specifically immunoreactive with," when referring to an antibody, refers to a binding reaction or interaction which is determinative of the presence of the analyte or epitope in a heterogeneous population of molecules such as proteins and other biological molecules. Thus, under designated immunoassay conditions, specified antibodies bind to a particular analyte or epitope and do not bind in a significant amount to other analytes or epitope present in the sample. A variety of immunoassay formats may be used to select antibodies specifically immunoreactive with a particular analyte or epitope. For example, solid-phase ELISA immunoassays are routinely used to select monoclonal antibodies specifically immunoreactive with a protein. See Harlow and Lane, *Antibodies, A Laboratory Manual*, CSHP, New York (1988), for a description of immunoassay formats and conditions that can be used to determine specific immunoreactivity.

The term "subject" as used herein refers to living multicellular vertebrate organisms, a category that includes both human and non-human mammals. The term "subject" includes both human and veterinary subjects.

When referring to cytokines or other biological materials, the term "steady state level" refers to the level of the cytokine or biological material produced in uninfected cells.

The term "synthetic polypeptide" refers to a polypeptide formed, in vitro, by joining amino acids in a particular order, using the tools of organic chemistry to form the peptide bonds.

A "transformed" cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

The term "vaccine" is used herein to mean a composition useful for stimulating a specific immune response in a vertebrate.

The term "vector" as used herein refers to a nucleic acid molecule as introduced into a host cell thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

III. Description of Several Embodiments

Provided herein in a first embodiment is an immunological assay method for detection of latent tuberculosis in a subject. Such methods include contacting a biological sample that may contain a first latency-specific binding partner (LSBP) from the subject with a corresponding LSBP, and detecting binding between the first LSBP and the corresponding LSBP, wherein such binding is indicative of latent tuberculosis in the subject. In some specific examples of these methods, the first LSBP is an antibody, and the corresponding LSBP is a latency-specific *M. tuberculosis* antigen (for instance, α-crystallin (Acr) or an immunogenic fragment thereof). In other specific examples of the methods, the first LSBP is a latency-specific *M. tuberculosis* antigen, and the corresponding LSBP is an antibody. In certain specific examples of the methods, the antigen is Acr or an immunogenic fragment thereof.

Another embodiment is a kit for the detection of latent tuberculosis in a subject. Such kits include at least one LSBP and instructions for carrying out an immunological assay method for detection of latent tuberculosis in a subject.

This disclosure also provides a method of eliciting an immune response in a subject. The methods include introducing into the subject an immune stimulatory amount of a *M. tuberculosis* latency-specific antigen or immunogenic fragment thereof, or a nucleic acid molecule encoding such an antigen (eg., Acr) or immunogenic fragment thereof. In certain specific examples, the method is a method of inhibiting or treating a latent tuberculosis infection in the subject. In particular examples of the methods, the elicited immune response results in decreased susceptibility of the subject to latent infection by *M. tuberculosis*.

This disclosure further provides a kit for eliciting an immune response in a subject. Such kits include an immune stimulatory amount of a *M. tuberculosis* latency-specific antigen or immunogenic fragment thereof, or a nucleic acid molecule encoding such an antigen or immunogenic fragment, and instructions for carrying out a method of eliciting an immune response in a subject. Particular examples of the kit include instructions for administering a component of the kit to a patient with a possible latent tuberculosis infection.

Further embodiments provide in vitro granulomas that include peripheral blood mononuclear cells, autologous macrophages, and mycobacteria. In such granulomas, the peripheral blood mononuclear cells are human peripheral blood mononuclear cells selected from the group consisting of *monocytes, B lymphocytes, T lymphocytes,* and combinations thereof. In certain examples of the granuloma, the mycobacteria are *M. tuberculosis*. Certain examples of the granuloma further include fibroblasts.

Also provided is a method for producing an in vitro granuloma, which method involves combining peripheral blood mononuclear cells, autologous macrophages, and mycobacteria in a low attachment container and incubating the combination for a sufficient amount of time to form the in vitro granuloma. In some, specific examples, fibroblasts are added to the combination. In some specific examples, exogenous cytokine(s) are added to the container in sufficient amount to enhance production of the in vitro granuloma. In some instances, the exogenous cytokine is IL-2, IFN-γ, TNF-α or a combination of two or more thereof.

Another embodiment provided herein is a method of screening a tuberculosis drug candidate for anti-tuberculosis therapeutic activity. Such methods include combining the drug with an in vitro granuloma comprising peripheral blood mononuclear cells, autologous macrophages, and mycobacteria, and determining whether the drug inhibits mycobacterial viability. In some specific examples, the peripheral blood mononuclear cells are human peripheral blood mononuclear cells selected from the group consisting of *monocytes, B lymphocytes, T lymphocytes,* and combinations thereof.

Still another embodiment provided herein is a method of screening a tuberculosis drug candidate for anti-tuberculosis therapeutic activity that includes combining the drug with an in vitro granuloma comprising peripheral blood mononuclear cells, autologous macrophages, and inactivated mycobacteria, and determining whether the drug inhibits reactivation of mycobacteria contained in the granuloma. In certain specific examples of the methods, the mycobacteria are *M. tuberculosis*.

Also provided is a method of screening a tuberculosis vaccine candidate that includes determining whether a mutant mycobacteria has a reduced ability, when compared against a wild type mycobacteria, to induce latency, survive, reactivate or induce granuloma necrosis in an in vitro granuloma comprising peripheral blood mononuclear cells, autologous macrophages, and the mutant mycobacteria. In some specific examples of the methods, the in vitro granuloma further comprises fibroblasts. In certain examples of the methods, the mutant mycobacteria includes a mycobacteria strain having a mutation in a latency gene. In other examples, the mutant mycobacteria is a *Mycobacterium tuberculosis* stain having a mutation in a gene selected from the group consisting of acr, a sigma factor gene, oxyR and aphC. In particular examples, the sigma factor gene is selected from the group consisting of sigF, sigC, and sigH.

Additional embodiments are kits for producing an in vitro granuloma, including a culture medium and instructions for carrying out a method of screening a tuberculosis vaccine candidate that includes determining whether a mutant mycobacteria has a reduced ability, when compared against a wild type mycobacteria, to induce latency, survive, reactivate or induce granuloma necrosis in an in vitro granuloma comprising peripheral blood mononuclear cells, autologous macrophages, and the mutant mycobacteria. In certain examples, the kit further includes a low attachment container and in certain specific examples, the kit further includes an amount of a cytokine.

IV. Production and use of the In Vitro Granuloma Model

This disclosure provides in this embodiment methods for producing and using an in vitro granuloma model, which model provides a consistent replicable, and reliable laboratory system. The in vitro granuloma can be used in many applications, for instance to study granuloma formation and maintenance, as well as to identify and characterize compounds that affect granuloma formation, maintenance, or reversion, and to study aspects of mycobacterial, including particularly mycobacterial latency.

In general, the in vitro granuloma is formed by combining peripheral blood mononuclear cells with macrophages and mycobacteria. The mixture of cells is incubated for a number of days to encourage formation of aggregates in the cell culture. Formation of the granulomas is further encouraged by use of low attachment containers in certain embodiments. After formation of cell aggregates, fibroblasts can optionally be added to the culture. In some embodiments, exogenous cytokines are added to the growth medium, for instance, IL-2, IFN-γ, and/or TNF-α, for instance prior to infection with mycobacteria.

By way of more specific example, autologous macrophages and mycobacteria are combined in one or more wells of a low attachment container, such as wells of a tissue culture dish treated to inhibit all attachment. Peripheral blood mononuclear cells (PBMCs), optionally $1 \times 10^6$ cells in a cell culture media (such as RPMI plus 10% human serum, HS (Lampire Biological Laboratories, Pipersville, Pa.)), are combined with the macrophages and mycobacteria and incubated at a temperature at which the cells will grow for between 5 and 7 days. When aggregates reach a diameter of approximately 1 mm, fibroblasts (optionally human lung fibroblasts) may be added.

Secretion of a variety of chemoattractant cytokines following phagocytosis of *M. tuberculosis* bacilli by the macrophage is important not only to the formation of the granuloma but also to its maintenance. Because of this, progression of the in vitro granuloma can be monitored by measuring cytokine levels. For cytokine analysis, supernatants are harvested, filter sterilized, and assayed by a known technique such as ELISA.

It is also beneficial in some embodiments to add exogenous cytokine to the medium, for instance during formation of the in vitro granuloma; in some instances, addition of cytokine enhances aggregate formation. By way of example, IL-2 (at 10 units/ml, for instance), IFN-γ (at 2 ng/ml, for instance), or TNF-α (at 50 ng/ml, for instance) (Endogen, Woburn, Mass.) or combinations of two or three cytokines are added to the cells prior to mycobacterial infection. When in vitro granulomas were maintained for longer periods of time, for instance for 9 days, cytokines could beneficially be added a second time. In some specific examples, the same amounts and kinds of cytokines were added at day 5 after starting the cultures.

Similarly, gene expression can be used to characterize the in vitro granuloma For RT-PCR or RPA analysis, aggregates are collected, washed and the RNA extracted. For histopathology, cells are fixed in a fixative, such as 10% formalin, and processed as tissue.

The in vitro granuloma model of the present disclosure has a variety of uses. For example, the in vitro granuloma model can be used to analyze and characterize the process of granuloma formation and granuloma necrosis. It can also be also used to characterize *M. tuberculosis* genes that are differentially expressed when the mycobacterium is located inside a granuloma versus when the mycobacterium in not located inside a granuloma.

The model, for instance when employed without the addition of exogenous cytokines, is useful to characterize native cytokine production by the cells composing a granuloma. In one embodiment, the cytokine levels produced by the in vitro granuloma model are compared to the steady state levels of the cytokines. The granuloma model is also useful for analyzing mycobacterial viability, as well as for pathophysiologic analyses.

V. Drug and Immune-Stimulating Compound Candidate Screening

The in vitro granuloma model described herein can be used for accurately screening candidate compounds, for instance, tuberculosis drug candidates. Methods of screening a tuberculosis drug candidate include adding the drug candidate to the in vitro granuloma model and determining whether the drug kills mycobacteria contained in the granuloma or otherwise alters the physiology of the bacilli or other cells in the granuloma. The model is optionally used to screen drugs for use in treating latent mycobacterial infections.

The in vitro granuloma model is also useful for screening immunostimulatory compounds, for example tuberculosis vaccine candidates. By way of example, the in vitro granuloma model is used as a precursor to animal studies, for instance to test mutant stains of *M. tuberculosis* that may be used as vaccines to prevent or reduce *M. tuberculosis* infection or the reactivation of latent mycobacterial infections. Animal study precursors help to reduce the costs and negative connotations associated with animal experimentation. Examples of the in vitro granuloma model provided herein are less expensive and much more rapid than conventional vaccine screening tests that rely on data generated from animal experiments.

A mutant *M. tuberculosis* strain can be constructed by methods known to those of skill in the art, for instance by inducing or screening for a mutation, such as a mutation in one of the latency genes selected from, but not limited to, acr, sigF, sigC, sigH, and other sigma factors, oxyR and aphC. Examples of methods known to those of skill in the art include in vitro mutagenesis and in vivo mutagenesis. The mutation can be a deletion of all or part of one or more of these latency genes or an insertion or substitution in one or more of these latency genes. When referring to mycobacterial strains in general or an *M. tuberculosis* strain specifically, the terms "mutated" and "mutant" refer to strains having one or more mutations that inhibit or prevent the strain from shifting down into a dormant or latent state, or that inhibit or prevent the strain from reactivating after shifting down into a dormant or latent state. Dormancy is a state of slow or stopped bacterial replication, but with some ongoing metabolism, whereas reactivation involves bacterial replication and log phase biochemistry.

In examples of methods for identifying mutated strains that can serve as vaccines, a mutated mycobacterial strain as described herein is added to the in vitro granuloma model in place of a wild-type mycobacteria strain. The efficacy of the mutated mycobacteria strain is determined based upon a reduced ability of the mutated strain to induce formation of a latent mycobacterial infection state, survive within the granuloma, reactivate from a latent state to an active state, and/or a reduced ability of the mutant strain to induce granuloma necrosis as compared to a wild-type mycobacterial strain. Cytokine production in the in vitro granuloma containing the mutated mycobacteria strain also can be analyzed and compared to cytokine production in a control in vitro granuloma model containing a wild-type mycobacteria strain.

VI. Identification of Latency-Specific Antigens

To gain insight into the molecular mechanisms of mycobacterial dormancy, and to provide molecules for detecting and/or tracking dormant infection, genes and proteins suspected of being involved in the adaptation to anoxia have been investigated. Results using reverse-transcription polymerase chain reaction (RT-PCR) technology (as described herein) have confirmed differential expression of various putative stress-response genes. Two of these genes that demonstrate increased activity in the anaerobic (shift-down) granuloma model are involved in oxidative stress response, oxyR and aphC (Dhadayauthapani et al., *J. Bacteriol.* 178: 3641–3649, 1996). The third encodes α-crystallin, an ATP-independent chaperon (Henriques et al., *J. Bacter.* 179: 1887–1897, 1997; Horwitz, *Proc. Nat'l. Acad. Sci. USA* 89:10449–10453, 1992), reported to be required for bacilli growth within macrophages (Yuan et al., *Microbiol.* 95, 16:9578–9583, 1998).

Latency-specific antigens in addition to those discussed in specific embodiments disclosed herein can be identified based on their preferential expression by latent mycobacteria, particularly *M. tuberculosis*, in comparison to mycobacteria that are not in latent phase. By way of example, differential expression can be detected using two dimensional gel electrophoresis of proteins extracted from latent and non-latent mycobacteria (e.g., bacteria cultured under anoxic conditions and aerobic conditions).

Alternatively, gene-chip (or cDNA microarray) analysis can be performed to detect preferential mRNA expression in latent (e.g., in vitro granuloma) versus non-latent (i.e., aerobic) cultures of mycobacteria. For instance, subtractive hybridization can be carried out by spotting all of the transcripts expressed in one culture or the other. The chip can then be probed using labeled (e.g., with a cyanine dye) latent and labeled non-latent mRNA (or cDNA) pools, and differential expression detected using known techniques.

The prototypical latency-specific antigen is α-crystallin; its identification and characterization is described in more detail herein.

VII. Detection of Latent Tuberculosis

It has been surprisingly found that latent *M. tuberculosis* can produce a high enough level of latency-specific antigens that such antigens, and/or antibodies reactive therewith, can be detected in subjects with latent *M. tuberculosis* infection.

With the demonstration herein that latent tuberculosis organisms produce specific antigens that elicit immunogenic responses in subjects, methods for the detection of latency-specific antigens, and/or antibodies to latency-specific antigens, and for the detection and/or diagnosis of latent infections, are now enabled.

Latency-specific antigens, or antibodies that recognize an epitope of a *M. tuberculosis* latency-specific protein (such as Acr) can be detected in samples from a subject, for instance serum or other biological fluid, using known immunological techniques. The presence of such latency-specific antigens or antibodies (e.g., circulating antibodies specific for an Acr epitope) indicates that the subject suffers from a latent tuberculosis infection.

Many techniques are commonly known in the art for the detection and quantification of antigen. Most commonly, purified antigen will be bound to a substrate, the antibody of the sample will bind via its Fab portion to this antigen, the substrate will then be washed and a second, labeled antibody will then be added which will bind to the Fc portion of the antibody that is the subject of the assay. The second, labeled antibody will be species specific, i.e., if the serum is from a human, the second, labeled antibody will be anti-human-IgG antibody. The substrate will then be washed and the amount of the second, labeled antibody that has been bound will be detected and quantified by standard methods.

Examples of methods for the detection of antibodies in biological samples, including methods employing dip strips or other immobilized assay devices, are disclosed for instance in the following patents: U.S. Pat. No. 5,965,356 (Herpes simplex virus type specific seroassay); U.S. Pat. No. 6,114,179 (Method and test kit for detection of antigens and/or antibodies); U.S. Pat. No. 6,077,681 (Diagnosis of motor neuropathy by detection of antibodies); U.S. Pat. No. 6,057,097 (Marker for pathologies comprising an autoimmune reaction and/or for inflammatory diseases); and U.S. Pat. No. 5,552,285 (Immunoassay methods, compositions and kits for antibodies to oxidized DNA bases).

By way of example, a microsphere assay (also called flow beads assays) also can be used to detect Acr protein or another LSA in biological fluids (such as a culture supernatant from an in vitro latency model, or biological samples from a subject). This technology, as represented by systems developed by Luminex Corporation and other systems developed by Becton Dickinson, allows one to process a very small amount of sample, typically 20 µl, to detect one or several analytes. The principle of this assay is based on the coupling of a "capture antibody" to microspheres containing specific amounts of a red dye and an infrared dye. After incubation of these microspheres with the sample, a secondary detection antibody coupled with biotin and streptavidin coupled with phycoerthrin (PE), the beads are analyzed with a flow cytometer. One laser detects the beads and a second one detects the intensity of the PE bound to those beads. This technology has been used to detect cytokines in multiplex assays, serotyping of *Streptococcus pneumonia*, simultaneous measurement of human chorionic gonadotropin (hCG) and alpha-fetoprotein (AFP), simultaneous detection of serum IgG to *Toxoplasma gondii*, Rubella virus, Cytomegalovirus, and Herpes Simplex Virus Types 1 and 2 (see technical notes available from Luminex Corp., for instance at their Web-site or through their catalog)

In certain embodiments, a polyclonal rabbit antiserum is used to capture the Acr protein on the microspheres. In some embodiments, the secondary detection antibody is a monoclonal antibody to Acr. Secondary antibodies used in such methods can be coupled to, for instance, biotin.

VIII. Production of Latency-Specific Immunological Binding Partners

Once a latency-specific *M. tuberculosis* protein is identified, it is advantageous to produce that protein, and/or antibodies that specifically recognize one or more epitopes on the protein, in sufficient amounts to be used in immunological or other assays. Methods for production of proteins, and antibodies reactive with identified proteins, are well known to those of ordinary skill in the art. The following methods are provided as representative examples, and should not be viewed as limiting.

A. Production of Proteins

Once a latency-specific protein is identified, it is a matter of well-known techniques to determine the sequence that encodes the protein. For instance, the entire coding sequence of the *M. tuberculosis* genome is known (Cole et al., Nature 393:537–544, 1998); this can be used to identify the gene that encodes an isolated latency-specific protein. The encoding sequence can then be used to produce quantities of protein in vitro.

One skilled in the art will understand that there are myriad ways to express a recombinant protein such that it can subsequently be purified. In general, an expression vector carrying the nucleic acid sequence that encodes the desired protein will be transformed into a microorganism for expression. Such microorganisms can be prokaryotic (bacteria) or eukaryotic (e.g., yeast). One appropriate species of bacteria is *Escherichia coli* (*E. coli*), which has been used extensively as a laboratory experimental expression system. Also, protein can be expressed using a viral (e.g., vaccinia) based expression system. Protein can also be expressed in animal cell tissue culture, and such a system will be appropriate where animal-specific protein modifications are desirable or required in the recombinant protein, or in one portion of a fusion protein.

Vectors suitable for stable transformation of culturable cells are also well known. Typically, such vectors include a multiple-cloning site suitable for inserting a cloned nucleic acid molecule, such that it will be under the transcriptional control of 5' and 3' regulatory sequences. In addition, transformation vectors include one or more selectable markers; for bacterial transformation this is often an antibiotic resistance gene. Such transformation vectors typically also contain a promoter regulatory region (e.g., a regulatory region controlling inducible or constitutive expression), a transcription initiation start site, a ribosome binding site, an RNA processing signal, and a transcription termination site, each functionally arranged in relation to the multiple-cloning site. For production of large amounts of recombinant proteins, an inducible promoter is preferred. This permits selective production of the recombinant protein, and allows both higher levels of production than constitutive promoters, and enables the production of recombinant proteins that may be toxic to the expressing cell if expressed constitutively.

In addition to these general guidelines, protein expression/purification kits are produced commercially. See, for instance, the QIAexpress™ expression system from QIAGEN (Chatsworth, Calif.) and various expression systems provided by InVitrogen (Carlsbad, Calif.). Depending on the details provided by the manufactures, such kits can be used for production and purification of latency-specific proteins.

One skilled in the art will understand that there are myriad ways to purify recombinant polypeptides, and such typical methods of protein purification may be used to purify latency-specific proteins. Such methods include, for instance, protein chromatographic methods including ion exchange, gel filtration, HPLC, monoclonal antibody affinity chromatography and isolation of insoluble protein inclusion bodies after over production. In addition, purification affinity-tags, for instance a six-histidine sequence, may be recombinantly fused or linked to the protein and used to facilitate polypeptide purification. A specific proteolytic site, for instance a thrombin-specific digestion site, can be engineered into the protein between the tag and the remainder of the fusion to facilitate removal of the tag after purification, if such removal is desired.

Commercially produced protein expression/purification kits provide tailored protocols for the purification of proteins made using each system. See, for instance, the QIAexpress™ expression system from QIAGEN (Chatsworth, Calif.) and various expression systems provided by InVitrogen (Carlsbad, Calif.). Where a commercial kit is employed to produce a functionalized TGF-β fusion protein, the manufacturer's purification protocol is a preferred protocol for purification of that protein. For instance, proteins expressed with an amino-terminal hexa-histidine tag can be purified by binding to nickel-nitrilotriacetic acid Ni-NTA) metal affinity chromatography matrix (*The QIexpressionist*, QIAGEN, 1997).

If the recombinant latency-specific protein is produced in a secreted form, e.g., secreted into the milk of a transgenic animal, purification can be from the secreted fluid. Alternatively, purification may be unnecessary if it is appropriate to apply the latency-specific protein directly to the subject in the secreted fluid (eg., milk), for instance to induce an immunological response in a subject.

B. Production of Antibodies

Monoclonal or polyclonal antibodies may be produced to *M. tuberculosis* latency-specific proteins, or to specific epitopes within such proteins. Optimally, antibodies raised against a latency-specific protein would specifically detect that protein. That is, such antibodies would recognize and bind the Acr protein and would not substantially recognize or bind to other proteins found in a biological sample. The determination that an antibody specifically detects its target latency-specific protein is made by any one of a number of standard immunoassay methods; for instance, the Western blotting technique (Sambrook et al, In *Molecular Cloning: A Laboratory Manual*, CSHL, New York, 1989).

To determine that a given antibody preparation (such as one produced in a mouse) specifically detects the target protein by Western blotting, total cellular protein is extracted from cells of a latent *M. tuberculosis* preparation, such as granulomas, and electrophoresed on a sodium dodecyl sulfate-polyacrylamide gel. The proteins are then transferred to a membrane (for example, nitrocellulose) by Western blotting, and the test antibody preparation is incubated with the membrane. After washing the membrane to remove non-specifically bound antibodies, the presence of specifically bound antibodies is detected by the use of an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the target latency-specific protein will, by this technique, be shown to bind to the target latency-specific protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-latency-specific protein binding.

Substantially pure latency-specific protein suitable for use as an immunogen is isolated from the transfected or transformed cells as described above. Concentration of protein in the final preparation is adjusted, for example, by concentration on an Amicon filter device, to the level of a few micrograms per milliliter. Monoclonal or polyclonal antibody to the protein can then be prepared as follows:

i. Monoclonal Antibody Production by Hybridoma Fusion

Monoclonal antibody to epitopes of a latency-specific protein identified and isolated as described (eg., Acr) can be prepared from murine hybridomas according to the classical method of Kohler and Milstein (*Nature* 256:495, 1975) or derivative methods thereof. Briefly, a mouse is repetitively inoculated with a few micrograms of the selected protein over a period of a few weeks. The mouse is then sacrificed, and the antibody-producing cells of the spleen are isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.* 70:419, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

ii. Polyclonal Antibody Production by Immunization

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988–991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 μM. Affinity of the antisera for the antigen is determined by preparing competitive binding curves, as described, for example, by Fisher (*Manual of Clinical Immunology*, Ch. 42, 1980).

iii. Antibodies Raised Against Synthetic Peptides

A third approach to raising antibodies against a latency-specific protein is to use synthetic peptides synthesized on a commercially available peptide synthesizer based upon the predicted amino acid sequence of the latency-specific protein.

By way of example only, polyclonal antibodies to specific peptides within Acr can be generated through well-known techniques by injecting rabbits with chemically synthesized peptide.

iv. Antibodies Raised by Injection of Latency-Specific Protein Encoding Sequence Antibodies may be raised against a latency-specific protein by subcutaneous injection of a DNA vector that expresses the latency-specific protein into laboratory animals, such as mice. Delivery of the recombinant vector into the animals may be achieved using a hand-held form of the Biolistic system (Sanford et al., *Particulate Sci. Technol.* 5:27–37, 1987) as described by Tang et al. (*Nature* 356: 152–154,1992). Expression vectors suitable for this purpose may include those that express the Z47 encoding sequence under the transcriptional control of either the human β-actin promoter or the cytomegalovirus (CMV) promoter.

Antibody preparations prepared against a latency-specific antigen or epitope of such are useful in quantitative immunoassays that determine concentrations of antigen-bearing substances in biological samples; they are also used semi-quantitatively or qualitatively to identify the presence of antigen in a biological sample, as described herein.

IX. Stimulation of Immunological Responses to Latent Tuberculosis

With the provision herein of antigens specific to latent tuberculosis infections, methods are now enabled for the stimulation of immune responses to such antigens in subjects. In certain embodiments, such immune responses will be protective against formation of latent tuberculosis infection in the subject. Latency-specific proteins (e.g., Acr) can be used, for instance, as immunogenic agents in the treatment, amelioration, or prevention of latent tuberculosis. Subjects selected for this type of treatment are those who are known to have, or are suspected of having or are at risk of suffering, a latent tuberculosis infection. An example of such a person is someone who has a positive tuberculin skin test, but has no or limited evidence of active disease (for example clinical symptoms such as fatigue, anorexia, weight loss, fever, nocturnal diaphoresis, cough, hemoptysis, or radiographic or other laboratory evidence recognized as indicative of active disease).

The provided immunostimulatory proteins or peptides, derived from latency-specific proteins (such as Acr) are combined with a pharmaceutically acceptable carrier or vehicle for administration as an immunostimulatory composition or a vaccine to human or animal subjects. In some embodiments, more than one protein or peptide fragment may be combined to form a single preparation.

The immunogenic formulations may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immunostimulatory agents or vaccines, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

The volume of administration will vary depending on the route of administration. By way of example, intramuscular injections may range from about 0.1 ml to 1.0 ml. Those of ordinary skill in the art will know appropriate volumes for different routes of administration.

The amount of protein in each vaccine dose is selected as an amount that induces an immunoprotective response without significant, adverse side effects. Such amount will vary depending upon which specific immunogen is employed and how it is presented. Initial injections may range from about 1 μg to 1 mg, with some embodiments having a range of about 10 μg to 800 μg, and still other embodiments a range of from approximately 25 μg to 500 μg. Following an initial vaccination, subjects may receive one or several booster immunizations, adequately spaced. Booster injections may range from 1 μg to 1 mg, with other embodiments having a range of approximately 10 μg to 750 μg, and still others a range of about 50 μg to 500 μg. Periodic boosters at intervals of 1–5 years, for instance three years, may be desirable to maintain the desired levels of protective immunity.

As described in WO 95/01441, the course of the immunization may be followed by in vitro proliferation assays of PBL (peripheral blood lymphocytes) co-cultured with ESAT6 or ST-CF, and especially by measuring the levels of IFN-released from the primed lymphocytes. The assays are well known and are widely described in the literature, including in U.S. Pat. Nos. 3,791,932; 4,174,384 and 3,949,064.

A recent development in the field of immune stimulatory compounds (e.g., vaccines) is the direct injection of nucleic acid molecules encoding peptide antigens (broadly described in Janeway & Travers, *Immunobiology: The Immune System In Health and Disease*, page 13.25, Garland Publishing, Inc., New York 1997; and McDonnell & Askari, *N. Eng. J. Med.* 334:42–45, 1996). Plasmids that include nucleic acid molecules described herein, or that include a nucleic acid sequence encoding an immunogenic peptide or peptide fragment of a latency specific polypeptide (such as Acr) or derived from a latency specific polypeptide (for instance, as a fusion protein, may be utilized in such DNA vaccination methods.

Thus, the terms "immunostimulatory preparation" and "vaccine" as used herein also include nucleic acid vaccines in which a nucleic acid molecule encoding a latency-specific polypeptide (such as Acr), or a fragment thereof is administered to a subject in a pharmaceutical composition. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264:16985, 1989), co-precipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992) and (Eisenbraun et al., *DNA Cell Biol.*

12:791, 1993), and in vivo infection using cloned retroviral vectors (Seeger et al., *Proc. Natl. Acad. Sci.* 81:5849, 1984).

Similarly, nucleic acid vaccine preparations can be administered via viral carrier.

It is also contemplated that the provided immunostimulatory molecules and preparations can be administered to a subject indirectly, by first stimulating a cell in vitro, which stimulated cell is thereafter administered to the subject to elicit an immune response.

X. Immunological and Pharmaceutical Compositions

Immunological compositions, including immunological elicitor compositions and vaccines, and other pharmaceutical compositions containing latency-specific polypeptides or antigenic fragments thereof are useful for reducing, ameliorating, treating, or possibly preventing mycobacterial infection, particularly latent *M. tuberculosis* infection. One or more of the polypeptides are formulated and packaged, alone or in combination with adjuvants or other antigens, using methods and materials known to those skilled in the vaccine art. An immunological response of a subject to such an immunological composition may be used therapeutically or prophylactically, and in certain embodiments provides antibody immunity and/or cellular immunity such as that produced by T lymphocytes such as cytotoxic T lymphocytes or $CD4^+$ T lymphocytes.

To enhance immunogenicity, one or more immunogenic polypeptides or fragments (e.g., haptens) may be conjugated to a carrier molecule. Immunogenic carrier molecules include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein-derived or non-protein-derived substances are known to those of ordinary skill in the art. An immunogenic carrier typically has a molecular weight of at least 1,000 Daltons, and in some embodiments greater than 10,000 Daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Alternatively, a multiple antigenic polypeptide comprising multiple copies of the protein or polypeptide, or an antigenically or immunologically equivalent polypeptide may be sufficiently antigenic to improve immunogenicity without the use of a carrier.

The latency-specific polypeptides may be administered with an adjuvant in an amount effective to enhance the immunogenic response against the conjugate. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. (*J. Immunol.* 147:410–415, 1991), encapsulation of the conjugate within a proteoliposome as described by Miller et al. (*J. Exp. Med* 176:1739–1744, 1992), and encapsulation of the protein in lipid vesicles may also be useful.

The compositions provided herein, including those formulated to serve as vaccines, may be stored at temperatures of from about −100° C. to 4° C. They may also be stored in a lyophilized state at different temperatures, including higher temperatures such as room temperature. The preparation may be sterilized through conventional means known to one of ordinary skill in the art. Such means include, but are not limited to filtration, radiation and heat. The preparations also may be combined with bacteriostatic agents, such as thimerosal, to inhibit bacterial growth.

A variety of adjuvants known to one of ordinary skill in the art may be administered in conjunction with the protein(s) in the provided vaccine composition. Such adjuvants include but are not limited to the following: polymers, co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; alum; QS 21, muramyl dipeptide; CpG oligonucleotide motifs and combinations of CpG oligonucleotide motifs; trehalose; bacterial extracts, including mycobacterial extracts; detoxified endotoxins; membrane lipids; or combinations thereof.

In a particular embodiment, a vaccine is packaged in a single dosage for immunization by parenteral (i.e., intramuscular, intradermal or subcutaneous) administration or nasopharyngeal (i.e., intranasal) administration. In certain embodiments, the vaccine is injected intramuscularly into the deltoid muscle. The vaccine may be combined with a pharmaceutically acceptable carrier to facilitate administration. The carrier is, for instance, water, or a buffered saline, with or without a preservative. The vaccine may be lyophilized for resuspension at the time of administration or in solution.

The carrier to which the polypeptide may be conjugated may also be a polymeric delayed release system. Synthetic polymers are particularly useful in the formulation of a vaccine to effect the controlled release of antigens.

Microencapsulation of the polypeptide will also give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters polyamides, poly-(d,l-lactide-co-glycolide) (PLGA) and other biodegradable polymers.

Doses for human administration of a pharmaceutical composition or a vaccine may be from about 0.01 mg/kg to 10 mg/kg, for instance approximately 1 mg/kg. Based on this range, equivalent dosages for heavier (or lighter) body weights can be determined. The dose may be adjusted to suit the individual to whom the composition is administered, and may vary with age, weight, and metabolism of the individual, as well as the health of the subject. Such determinations are left to the attending physician or another familiar with the subject and/or the specific situation. The vaccine may additionally contain stabilizers or physiologically acceptable preservatives, such as thimerosal (ethyl(2-mercaptobenzoate-S)mercury sodium salt) (Sigma Chemical Co., St. Louis, Mo.).

XI. Kits

Kits are provided which contain the necessary reagents for growing in vitro granulomas or for determining the presence (or absence) of a latency-specific antigen and/or antibody in a biological sample, using an immunological binding reaction. Instructions provided in the diagnostic kits can include calibration curves, diagrams, illustrations, or charts or the like to compare with the determined (e.g., experimentally measured) values or other results.

A. Kits for Growing In Vitro Granulomas

Kits for growing in vitro granulomas include, for instance, cell culture media (e.g. RPMI plus 10% human serum, HS) and optionally may include a low attachment container (e.g., a tissue culture dish treated to inhibit all attachment), a filter, and/or a fixative. Specific examples of such kits also include an amount of one or more cytokine, for instance IL-2, IFN-γ, and/or TNF-α. Reagents supplied in the kits may be contained in separate containers.

The kits may also include means for granuloma analysis, for instance ELISA reagents, reagents for RT-PCR, and/or RPA reagents, which may also be provided in some kits in one or more separate containers. Cell culture, ELISA, RT-PCR, and RPA techniques are well known to those of ordinary skill in the art.

Reaction vessels and auxiliary reagents such as buffers, enzymes, etc. may also be included in the kits.

Additional components in some kits include instructions for carrying out the cell culture and/or subsequent analysis. Where provided, instructions may allow the tester to grow in vitro granulomas and use them to identify latency-specific antigens and screen drugs and immunostimulatory compounds, such as vaccines.

B. Kits for Detection of Latency-Specific Antigen

Kits for the detection of latency-specific $M.$ $tuberculosis$ protein expression include for instance at least one target protein specific binding agent (e.g., a polyclonal or monoclonal antibody or antibody fragment) and may include at least one control. The latency-specific protein specific binding agent and control may be contained in separate containers. The kits may also include means for detecting target protein agent complexes, for instance the agent may be detectably labeled. If the detectable agent is not labeled, it may be detected by second antibodies or protein A, for example, which may also be provided in some kits in one or more separate containers. Such techniques are well known.

Additional components in some kits include instructions for carrying out the assay. Instructions will allow the tester to determine whether latency-specific protein expression levels are altered, for instance in comparison to a control sample. Reaction vessels and auxiliary reagents such as chromogens, buffers, enzymes, etc. may also be included in the kits.

By way of example only, an effective and convenient immunoassay kit such as an enzyme-linked immunosorbent assay can be constructed to test anti-Acr antibody in human serum. Expression vectors can be constructed using the Acr cDNA to produce the recombinant Acr protein in either bacteria or baculovirus (as described above). By affinity purification, unlimited amounts of pure recombinant latency-specific protein (such as Acr) can be produced.

C. Kits for Detection of Antibody to Latency-Specific Antigens

Other examples of assay kits provide a recombinant latency-specific protein as an antigen and enzyme-conjugated goat anti-human IgG as a second antibody. Examples of such kits also can include one or more enzymatic substrates. Such kits can be used to test if a biological sample from a subject contains antibodies against a latency-specific protein.

The disclosure is further illustrated by the following non-limiting Examples.

EXAMPLES

Example 1

Preparation and Characterization of an In Vitro Granuloma Model

The principal defense of the human host against a mycobacterial infection is the formation of granulomas, which are compact organized collections of activated macrophages, including epithelioid and multinucleated giant cells, surrounded by $T$ $lymphocytes,$ and later by fibroblasts and collagen that aggregate around the macrophage-core. The granuloma may prevent active (non-latent) disease by sequestering the invading organisms. If the granuloma is maintained, these bacteria may remain latent for many years.

To study this process of granuloma formation and the granuloma's subsequent breakdown when host defenses are compromised, an in vitro model was developed. This example provides a description of one method for producing the in vitro granuloma that can be used as a model system, as well as several methods used to characterize the model. In overview, human peripheral blood mononuclear cells, autologous macrophages and mycobacteria were combined in low attachment tissue culture dishes. The resulting aggregates were characterized using microscopy and immunohistochemical staining. Cytokine production was assessed by ELISA and bacterial mRNA detected by RT-PCR.

Peripheral blood mononuclear cells ($1\times10^6$), autologous macrophages ($1\times10^6$) and mycobacteria ($1\times10^1$) were combined in low attachment tissue culture dishes (COSTAR™ Ultra Low Attachment Clusters, Costar Corp., Cambridge, Mass.) and incubated at 37° C. in 5% $CO_2$. Human peripheral blood mononuclear cells (PBMCs, $1\times10^6$ cells in RPMI plus 10% HS) were added after 24 hours, and the mixture incubated for 5–7 days. Aggregate formation was observed. Human lung fibroblasts (from the cell line 33Lu) were added when the aggregates were approximately 1 mm in diameter.

Figure 1:
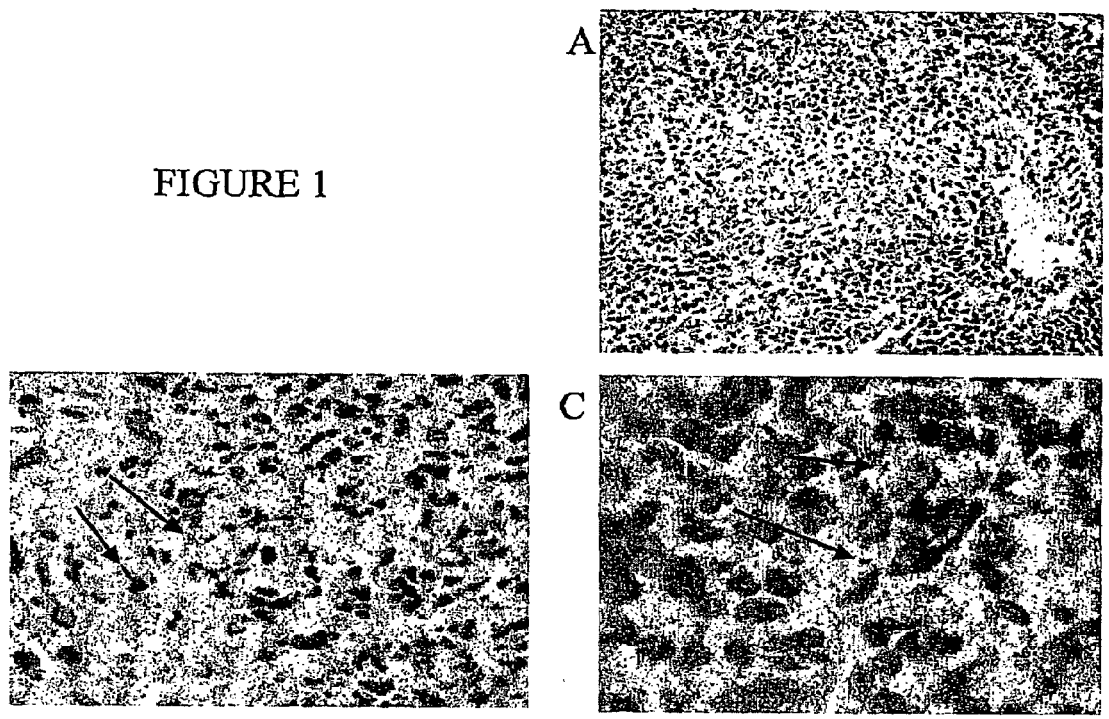
FIG. 1 is a series of micrographs of aerosol-infected guinea pig lung granuloma tissue.

The aggregates were characterized using microscopy and immunohistochemical staining with standard methodology. Small, rounded aggregate structures were formed in the cultures, which developed more defined edges with the addition of human lung fibroblasts. Microscopic examination of these aggregates using immunostaining found $CD68^+$ epithelioid macrophages and sparse, small round $CD3^+$ lymphocytes than in complex, resembled small granulomas seen in clinicopathologic specimens. Acid-fast staining bacteria were observed within and between the cells composing the granulomas (FIG. 1).

In addition to morphology, cytokine production was assessed by ELISA. In particular, cytokines that are known to be upregulated during early stage $M.$ $tuberculosis$ infection were analyzed.

By 24 hours following infection, the aggregates were found to generate levels of TNF, IL-8, and IL-6 that were elevated well above levels found in uninfected control cells. After 48 hours levels of IFN were likewise increased above controls. This elevated cytokine production continued over the nine day duration of the experiment. Results also indicate increased levels of IL-2 and IL-12, peaking at 48 hours, but remaining above control levels throughout the course of the experiment. All of these cytokines are detected at significantly higher levels in tuberculosis patients when compared to healthy controls.

Example 2

Detection of Differential Transcription of Acr mRNA in a Granuloma Model

Using bacteria cultured in an anoxic chamber, *M. tuberculosis* genes were identified that were differentially expressed after much of the available oxygen had been utilized. The genes that were differentially expressed were acr, sigF, oxyR and aphC. Of these four genes, acr encodes a protein (α-crystallin) that is secreted by the Mycobacterium.

In order to confirm that these genes are expressed in the in vitro granuloma model, RT-PCR and RNA protection assays were performed. These assays showed that mRNA from mycobacterial genes acr, aphC, and sigF were transcribed. These transcripts were not found in uninfected in vitro granuloma controls.

Figure 2:
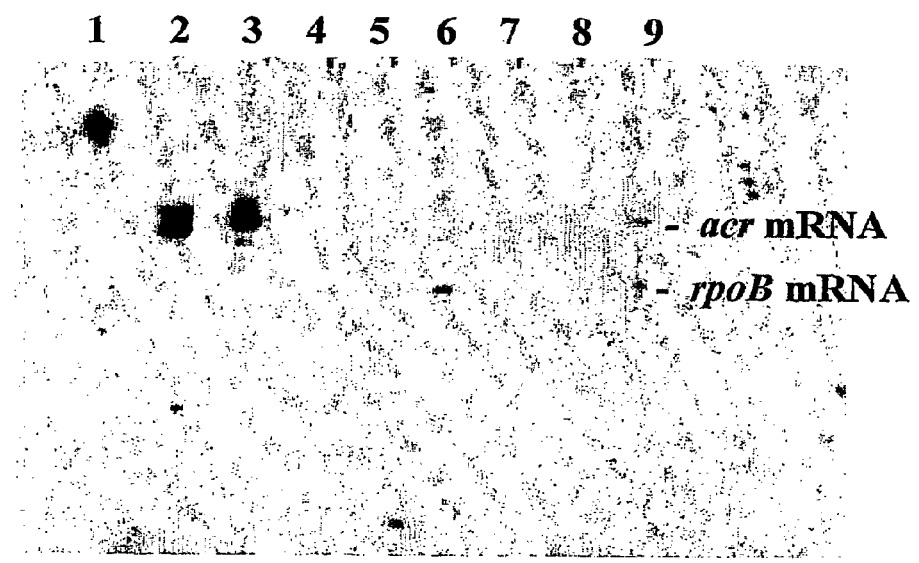
FIG. 2 is a ribonuclease protection assay (RPA) blot. Lanes 1–5 are various negative and positive controls, as indicated. Lanes 6–9 represent hybridizations to mRNA from mycobacteria grown 5 or 7 days either aerobically or in the anoxic chamber. Acr mRNA was observed at all four time points while rpoB mRNA was only observed in aerobically grown cultures.
Figure 3:
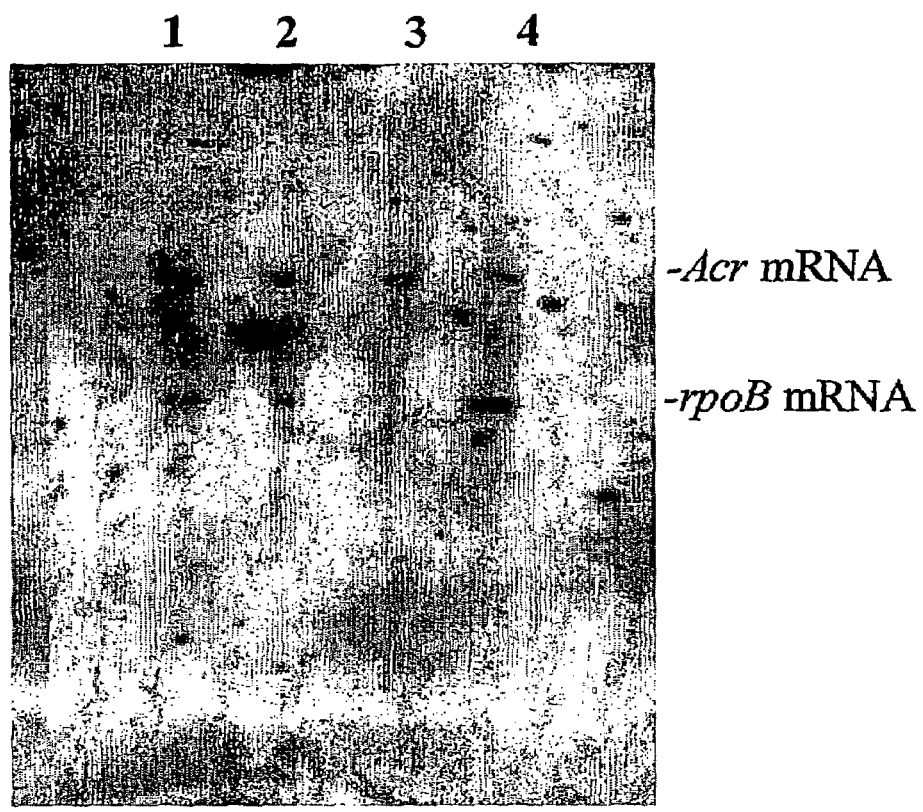
FIG. 3 is a RPA blot. Lanes 1 and 2 represent hybridizations to mRNA from mycobacteria extracted after 7- or 12-day incubations in the in vitro granuloma model. Both acr and rpoB mRNA were observed at both time points, likely indicating that aerobic bacilli were present in the granuloma. Lanes 3 and 4 are positive controls; acr mRNA and acr and rpoB DNA, respectively.

Typical results from representative experiments are shown in FIGS. 2 and 3, which are ribonuclease protection assay (RPA) blots. In FIG. 2, acr mRNA was observed at all four time points while RpoB mRNA was only observed in aerobically grown cultures. In FIG. 3, acr and RpoB mRNA were observed both at 7- or 12-day incubations in the in vitro granuloma model, which is believed to indicate that aerobic bacilli were present in the granuloma

Example 3

Other In Vitro Latency Models

The following example provides other in vitro latency models, which can be used, for example, to confirm results obtained with the in vitro granuloma model (e.g., to screen drugs and immunostimulatory compounds and to identify latency-specific antigens).

Guinea Pig Aerosol Infection Model

When infected by aerosol inoculation using a small number of *M. tuberculosis* bacilli, it was observed that the bacteria cause formation of granulomas associated with the epithelial pneumocytes in the deep alveoli of the lung. Though these granulomas apparently are not able to completely contain the infection, and the bacteria eventually overwhelm this animal, there are a number of similarities with human granulomas. For example, these granulomas center on necrotic areas and contain predominantly macrophages, including epithelioid and multinucleated giant cells and *T lymphocytes*. Differential transcription of the bacterial Acr gene has been detected in these granulomas.

In Vitro Anoxic Chamber Models

Wayne and Hayes developed an in vitro persistence model that subject *M. tuberculosis* bacilli to gradual oxygen deprivation by incubation in sealed containers with controlled agitation (Wayne and Hayes, *Infect. Immun.* 64:2062–2069, 1996). Growth under these conditions can be operationally divided into two non-replicating persistent (NRP) states: a microacrophilic state associated with induction of glycine dehydrogenase activity (NRP1), and a subsequent lower oxygen state (NRP2), in which glycine dehydrogenase activity declines and alterations in drug susceptibility are manifest. Specifically, cells become resistant to ciprofloxicin and sensitive to metronidazole, possible due to changes in DNA superhelicity and cell permeability, respectively (Wayne and Hayes, *Infect. Immun.* 64:2062–2069, 1996). These observations correlate with the intractability of clinical TB to single antibiotic therapy (Dickinson and Mitchison, *Am. Rev. Respir. Dis.* 123:367–371, 1981).

A modified version of this sealed vessel has been developed (FIG. 5), which allows monitoring of several environmental growth conditions (including optical density culture population, oxygen concentration, pH, and assaying of enzymes induced only under low oxygen tension), as well as providing containment of the pathogen and easy nucleic acid harvest by direct centrifugation of the vessel. Using this system, it has been shown that *M. tuberculosis* bacilli cease to replicate but remain metabolically active for several months under conditions of low oxygen (FIG. 12).

Example 4

Construction of Acr-FLAG Fusion Proteins

Oligonucleotide primers for polymerase chain reaction (PCR) were designed and generated. These primers were designed to allow the amplification of the hspX gene from *M. tuberculosis* (encoding Acr) with the addition of the FLAG (Sigma) epitope tag fused to amino- or carboxyterminus of Acr depending on which primer pair was used. Primer design also included the introduction of restriction endonuclease recognition sites to facilitate subsequent recombinant DNA methodologies involved in cloning and expression of these amplified sequences. Sequences of the primers to generate the N-terminal FLAG-Acr fusion were SEQ ID NO: 1 and SEQ ID NO: 2. Sequences of the primers to generate the C-terminal Acr-FLAG fusion were SEQ ID NO: 3 and SEQ ID NO: 4.

PCR reactions were performed using one microgram MTB H37Rv genomic DNA as template and 20 mM Tris-HCl, pH 8.4, 50 mM KCl, 1.5 mM $MgCl_2$, and 2.5 units AmpliTaq (Gibco BRL) thermostable DNA polymerase. PCR was performed with the following cycle parameters: 94° C., 5 minutes (1×), 94° C., 1 minute; 55° C., 30 seconds; 72° C., 2.5 minutes (2×), 94° C., 1 minute; 60° C., 30 seconds; 72° C., 2.5 minutes (30×), 72° C., 7 minutes (1×). Following PCR amplification the amplified DNA fragments were purified and digested by restriction endonuclease, and ligated into likewise digested plasmid vector pMV261.1. Following ligation, the reactions were transformed into *E. coli* and positive colonies selected by antibiotic resistance. Selected colonies were screened for the presence of the recombinant insert by PCR, and sequence verification was achieved by DNA sequencing of each positive clone. Positive N-terminal and C-terminal Act-FLAG fusion plasmids were subsequently transformed into both *M. smegmatis* and *M. tuberculosis* and transformed colonies selected by antibiotic resistance.

Expression of the fusion proteins was confirmed by Western blotting; representative blots are shown in FIG. 6 (N-terminal fusion) and FIG. 7 (C-terminal fusion).

Example 5

Immunoprecipitation of Acr

Acr-FLAG fusion proteins were immunoprecipitated with a FLAG Immunoprecipitation Kit acquired from Sigma according to the manufacturer's instructions. Native Acr immunoprecipitations were performed on mycobacterial lysates using sepharose CL4B beads (Pharmacia) to which polyclonal rabbit antibodies generated against Acr had been conjugated according to the manufacturer's instructions. Briefly, a pre-clearing step was performed to remove any proteins from the lysate that might non-specifically bind to the sepharose beads. This was accomplished by adding 50 μl of unconjugated sepharose to 975 μl of TSA (0.01M Tris-HCl, pH 8; 0.14M NaCl; 0.025% NaN$_3$) and 16 μl of MTB lysate (2.3 mg/mL) in a 1.5 mL microfuge tube. The solution was incubated for one hr at 4° C. with constant rocking. The solution was then centrifuged for 5 sec at 14,000 rpm to pellet the sepharose and the supernatant removed and transferred to a new microfuge tube. 25 μl of anti-Acr antibody conjugated sepharose beads were added to the supernatant and incubated for one hour at 4° C. with constant rocking. The solution was then centrifuged as previously described and the supernatant was removed and discarded. The sepharose pellet was then washed 4 times with 1 mL each of 1) 0.1% Triton X-100 in TSA, 2) 0.1% Triton X-100 in TSA, 3) TSA, 4) 0.05M Tris-HCl, pH 6.8. Addition of each solution was followed by resuspension of the sepharose pellet, a 5-second centrifugation to repellet the sepharose, and removal of the wash supernatant. Finally, 40 μl of 2× gel loading buffer (Novex) was added to the sepharose pellet, and the suspension incubated for 1.5 hours at 56° C. A final centrifugation was performed to re-pellet the sepharose and the supernatant (containing the immunoprecipitated Acr protein) was removed and saved for analysis by Western blot.

Example 6

Western Blot

Immunoprecipitated Acr samples or mycobacterial lysates were resolved by sodium dodecyl sulfate polyacrylamide gel electrophoresis (SDS PAGE) with pre-cast 4–12% bis-Tris polyacrylamide gradient gels (Novex) for one hour at 200 volts constant. Following electrophoresis, the resolved proteins were transferred to a pre-cut 0.2-micron polyvinylidene difluoride membrane (PVDF, Novex) according to the manufacturer's instructions by electrocapillary transfer at 150 milliamps constant for one hour. Dried membranes were prepared for Acr detection by immersion in methanol and unconjugated PVDF surfaces were blocked by incubation of the membrane in TBS Tween 20 containing 3% gelatin (BioRad) for one hour with constant rocking. The membrane was then washed 3 times for 10 minutes each with TBS+Tween 20 with constant rocking.

Detection of Acr was accomplished by incubation of the membrane with a 1 to 5,000 dilution of polyclonal rabbit antibodies generated against Acr, or a 1:20,000 anti-FLAG M2 monoclonal antibody, (Sigma), or a 1 to 250 dilution of rabbit anti-phosphotyrosine antibody (Zymed) in TBS+Tween 20 containing 1% gelatin for one hour with constant rocking. Subsequently, the membrane was washed as described above. A one-to-10,000 dilution of biotinylated goat-anti-rabbit IgG in TBS+Tween 20 with 1% gelatin was then applied to the blot, and incubated for one hour with constant rocking. Subsequently, the blot was washed as described above. A final incubation of the blot with a 1 to 10,000 dilution of a streptavidin-alkaline phosphatase (AP) conjugate in TBS+Tween 20 was incubated with the blot for 30 minutes with constant rocking. Detection of the presence of AP was accomplished by the incubation of the blot in a solution of NBT+BCIP (Novex). The incubation was halted when the desired level of color development was achieved, and stopped by extensive washing of the blot in water. Blots were dried for archiving.

FIG. 8 shows five strips cut from a Western blot prepared as described of whole cell mycobacteria cell lysates; the arrows indicate the location of recombinant Acr protein. The strips were developed with the indicated primary antibodies. In addition to the control antibody, this blot demonstrates the presence of tyrosine phosphorylation in the final strip.

FIG. 9 shows two Western blots prepared as described from culture supernatants of *M. tuberculosis* bacilli grown under the conditions indicated in the Brief Description of the Figures. FIG. 9A was probed using rabbit anti-Acr antibody; FIG. 9B is a control blot Acr protein is detected in 7 day and 12 month anoxic cultures and in vitro granuloma. Lower molecular weight variants are observed in the 12 month and in vitro granuloma supernatants. For comparison, FIG. 11 shows s a Coomassie stained SDS-PAGE gel of culture supernatants from *M. tuberculosis* bacilli cultured under the indicated conditions.

Example 7

2-Dimensional Gel Electrophoresis

Lysates of *M. smegmatis* and *M. tuberculosis* carrying the Acr-FLAG fusion plasmids were prepared. Bacterial suspension cultures were pelleted by centrifugation (5,000 rpm, 10 minutes) and the bacterial pellet washed with phosphate buffered saline (PBS). Pellets were then resuspended in 1 mL of 9M urea and the suspension transferred to 2 mL microfuge tubes containing approximately 200 μl of 0.1 mm diameter glass beads (Biospec products). The cells were then lysed by rapid shaking (three times, one minute each) in a Minibeadbeater Biospec products). Following lysis, the cellular debris and glass beads were pelleted by centrifugation and the supernatant removed. Protein quantification was performed using the colorimetric BioRad protein assay (BioRad).

For resolution of the protein sample in the first dimension, 150 micrograms of protein was added to 92.5 μl of solubilization buffer (9M Urea, 140 mM DTT, 4% Triton X-100) and brought to a final volume of 185 μL with 9M urea. The suspension was incubated for one hour with constant rocking at room temperature. Following this incubation, 1 μl Biolytes electrolyte solution (BioRad, 0.2% final), and several crystals of Bromophenol Blue (Fisher) were added. Hydration of the IPG strips and application of the protein solution to the strips was carried out overnight in a IPG strip hydration apparatus (Pharmacia). Following hydration the strips were subjected to electrophoresis in a LKB MultiPhor II apparatus (Pharmacia) using a Pharmacia EPS 3500 XL electrophoresis apparatus with the following parameters: 350V, 30 minutes, 350V–3500V (1.5 hour gradient), 3500V, 3.5 hours, to give a final running time of 15,200 Volt-hours.

For running the second dimension, the resolved IPG strips were equilibrated in equilibration buffer (6M Urea, 0.375M Tris, pH 8.8, 2% SDS, and 20% Glycerol) containing 2% w/v DTT (10 minutes) and 2.5% iodoacetamide (10 minutes). The equilibrated strips were resolved on Criterion (BioRad) 8–16% polyacrylamide gels according to the manufacturer's instructions for one hour at 200 volts constant.

FIG. 10 is a representative two-dimensional gel electrophoresis analysis of a sample taken from *M. tuberculosis* grown under anoxic conditions. Acr protein is indicated by the circle.

Example 8

Detection of Acr

Using polyclonal antibodies produced against the cloned *M. tuberculosis* Acr protein, secreted bacterial Acr was-detected in culture supernatants from anoxic chamber and the in vitro granuloma model (FIG. 9). Polyclonal antiserum to Acr protein was also used to detect mycobacteria in aerosol infected guinea pig lung granuloma tissue (FIG. 1C).

Figure 4:
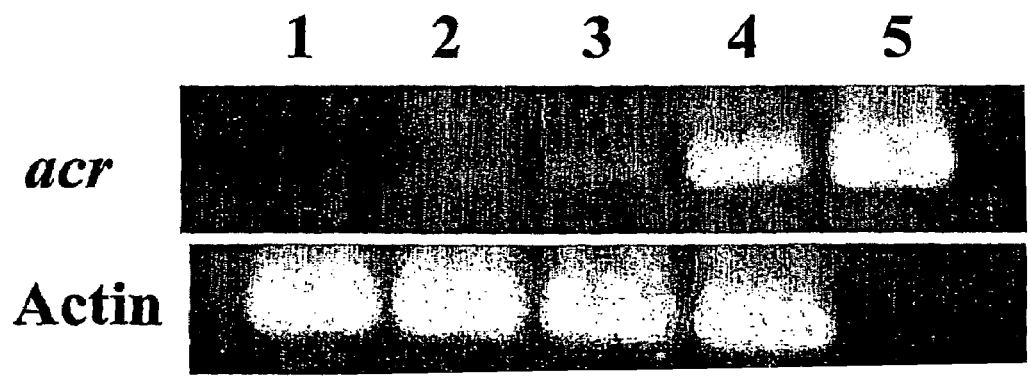
FIG. 4 is a pair of agarose gels, showing the results of RT-PCR. Acr transcript is clearly induced with longer infection in the in vivo model (lanes 2, 3, and 4), and is even more strongly induced in anoxic culture (lane 5).

Acr protein was detected in supernatants and cell lysates from anoxic but not aerobic grown *M. tuberculosis* (FIG. 9). Acr was immunoprecipitated from *M. tuberculosis* lysates. Changes in molecular weight of Acr were detected in anoxic or infected in vitro granulomas but not aerobic grown cultures (FIG. 9). *M. tuberculosis* acr mRNA was detected in anoxic but not aerobic cultures and acr and eukaryotic actin mRNA in infected but not uninfected control guinea pig lungs (FIG. 4).

This disclosure provides an in vitro granuloma model and methods of use, as well as immunological methods for the detection of latent tuberculosis in a subject. The in vitro granuloma model can be used, for example, to identify latency-specific antibodies and to screen drugs and immunostimulatory compounds. The immunological methods can include, for example, using a latency-specific *M. tuberculosis* antigen to detect a corresponding antibody from the subject, or using an antibody to detect the latency-specific antigen. The disclosure further provides methods for identifying latency-specific antigens (and their corresponding antibodies) for use in such methods, and specific latency-specific antigens such as α-crystallin. It will be apparent that the precise details of the methods described may be varied or modified without departing from the spirit of the described disclosure. We claim all such modifications and variations that fall within the scope and spirit of the claims below.

---

We claim:

1. An immunological assay method for detection of latent tuberculosis in a subject, comprising
    contacting a biological sample from the subject with a latency-specific binding partner (LSBP), wherein the biological sample may contain a latency-specific antigen, which latency-specific antigen is α-crystallin or an immunogenic fragment thereof; and
    detecting binding between the LSBP and the latency-specific antigen thereby detecting latent tuberculosis in the subject.

2. The method of claim 1, wherein the LSBP is an antibody or fragment thereof.

3. The method of claim 1, wherein the biological sample comprises a biological fluid sample.

4. An in vitro granuloma comprising peripheral blood mononuclear cells, autologous macrophages, and mycobacteria, wherein the mycobacteria are selected from the group consisting of, *M. tuberculosis, M. avium*, and *M. smeginatis*.

5. The in vitro granuloma of claim 4, wherein the peripheral blood mononuclear cells are human peripheral blood mononuclear cells selected from the group consisting of *monocytes, B lymphocytes, T lymphocytes,* and combinations thereof.

6. The in vitro granuloma of claim 4, wherein the mycobacteria are *M. tuberculosis*.

7. The in vitro granuloma of claim 4, further comprising fibroblasts.

8. The in vitro granuloma of claim 4, wherein the macrophages comprise autologous macrophages.

9. The in vitro granuloma of claim 8, wherein the macrophages comprise autologous macrophages, and wherein the myczobacteria are *M. tuberculosis*.

10. A method for producing an in vitro granuloma comprsing combining peripheral blood mononuclear cells, autologous macrophages, and mycobacteria in a low attachment container and incubating the combination for a sufficient amount of time to form the in vitro granuloma, wherein the mycobacteria are selected from the group consistina of *M. tuberculosis, M. avium*, and *M. smegmatis*.

11. The method of claim 10, wherein fibroblasts are added to the combination.

12. The method of claim 10, further comprising adding exogenous cytokine to the container in sufficient amount to enhance production of the in vitro granuloma.

13. The method of claim 12, wherein the exogenous cytokine is IL-2, IFN-γ, TNF-α, or a combination of two or more thereof.

14. The method of claim 10, wherein the peripheral blood mononuclear cells are human peripheral blood mononuclear cells selected from the group consisting of *monocytes, B lymphocytes, T lymphocytes,* and combinations thereof.

15. The method of claim 10, wherein the mycobacteria are *M. tuberculosis*.

16. The method of claim 10, wherein the macrophages comprise autologous macrophages.

17. A method of screening a tuberculosis drug candidate for anti-tuberculosis activity comprising combining the drug with an in vitro granuloma comprising peripheral blood mononuclear cells, autologous macrophages, and mycobacteria, and determining whether the drug inhibits mycobacterial viability, wherein the mycobacteria are selected from the group consisting of *M. tuberculosis, M. avium*, and *M. smegmatis*.

18. The method of claim 17, wherein the in vitro granuloma further comprises fibroblasts.

19. The method of claim 17, wherein the peripheral blood mononuclear cells are human peripheral blood mononuclear cells selected from the group consisting of *monocytes, B lymphocytes, T lymphocytes,* and combinations thereof.

20. The method of claim 17, wherein the macrophages comprise autologous macrophages.

21. A method of screening a tuberculosis drug candidate for anti-tuberculosis activity comprising combining the drug with an in vitro granuloma comprising peripheral blood mononuclear cells, autologous macrophages, and inactivated mycobacteria, wherein the mycobacteria are selected from the group consisting of *M. tuberculosis, M. avium*, and *M. smegmatis*, and determining whether the drug inhibits reactivation of mycobacteria contained in the granuloma.

22. The method of claim 21, wherein the macrophages comprise autologous macrophages.

23. A method of identifying a mutant mycobacterium with a reduced ability to enter a latent state or to reactivate from a latent state, comprising determining whether the mutant mycobacterium has a reduced ability, as compared to its wild type form, to induce latency, survive, reactivate or induce granuloma necrosis in an in vitro granuloma comprising peripheral blood mononuclear cells, autologous macrophages, and the mutant mycobacterium, wherein the mutant mycobacterium and the wild-type mycobacterium are selected from the group consisting of *M. tuberculosis, M. avium*, and *M. smegmatis*.

24. Tho method of claim 23, wherein the mutant mycobacteria comprises a mycobacteria strain having a mutation in a latency gene.

25. The method of claim 23, wherein the mutant mycobacteria is a *Mycobacteriwn tuberculosis* strain having a mutation in a gene selected from the group consisting of acr, a sigma factor gene, oxyR and aphC.

26. The method of claim 25, wherein the sigma factor gene is selected from the group consisting of sigF, sigC, and sigH.

27. The method of claim 23, wherein the macrophages comprise autologous macrophages.

* * * * *

UNITED STATES PATENT AND TRADEMARK OFFICE
CERTIFICATE OF CORRECTION

PATENT NO.        : 7,105 170 B2
APPLICATION NO. : 10/250930
DATED             : September 12, 2006
INVENTOR(S)       : Quinn et al.

It is certified that error appears in the above-identified patent and that said Letters Patent is hereby corrected as shown below:

In column 6, line 49, "form oral washing" should be --from oral washing--.
In column 6, line 50, "amount normal" should be --amount of normal--.
In column 7, line 23, "human peripheral blood mononuclear cells" (PBMCs) should be --"human peripheral blood mononuclear cells (PBMCs)"--.
In column 7, line 39, "In" should be --in--.
In column 11, line 26, "Appt Math" should be --Appl. Math.--.
In column 11, line 48, "Tm" should be --$T_m$--.
In column 13, line 45, "epitope" should be --epitopes--.
In column 16, line 62, "granuloma For" should be --granuloma. For--.
In column 19, line 50, "catalog)" should be --catalog).--
In column 21, line 11, "acid Ni-NTA)" should be --acid (Ni-NTA)--.
In column 22, line 49, "(about 12 $\mu$M." should be -- (about 12 $\mu$M).--.
In column 24, lines 51-52, "protein, may" should be --protein), may--.
In column 24, line 67 through column 25, line 1, "1992) and (Eisenbraun et al." should be --1992 and Eisenbraun et al.--.
In column 28, line 48, "than" should be --that--.
In column 28, line 58, "that-were" should be --that were--.
In column 32, line 12, "blot Acr" should be --blot. Acr--.
In column 32, line 16, "shows s" should be --shows--.

In Claim 1 (Col. 35, line 2), "comprising" should be --comprising:--.
In Claim 9 (Col. 35, line 33), "myczobacteria" should be --mycobacteria--.
In Claim 10 (Col. 35, lines 34-35), "comprsing" should be --comprising--.
In Claim 25, (Col. 36, line 45), "*Mycobacteriwn*" should be --*Mycobacterium*--.

Signed and Sealed this

Twenty-seventh Day of March, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 54
<212> TYPE: DNA
<213> ORGANISM: Artificial sequence
<220> FEATURE:
<223> OTHER INFORMATION: Synthetic oligonucleotide

<400> SEQUENCE: 1
cgcggatcca gattataaag atgatgatga taaaatggcc accacccttc ccgt        54

<210> SEQ ID NO 2
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 2
cgcggatcct cagttggtgg accggatctg aat        33

<210> SEQ ID NO 3
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 3
cgcggatcca atggccacca cccttcccg        29

<210> SEQ ID NO 4
<211> LENGTH: 57
<212> TYPE: DNA
<213> ORGANISM: Artificial sequence
<220> FEATURE:
<223> OTHER INFORMATION: Synthetic oligonucleotide

<400> SEQUENCE: 4
cgcggatcct catttatcat catcatcttt ataatcgttg gtggaccgca tctgaat        57